(12) United States Patent
Oh et al.

(10) Patent No.: US 7,163,698 B2
(45) Date of Patent: *Jan. 16, 2007

(54) CONTROLLED DRUG DELIVERY SYSTEM USING THE CONJUGATION OF DRUG TO BIODEGRADABLE POLYESTER

(76) Inventors: Jong Eun Oh, #27-804 Hanshin 3rd Apartment, Banpo 2-dong, Socho-ku, Seoul, 137-767 (KR); Keon Hyoung Lee, A-401 Green Villan 81-12, Seongsan-dong, Mapo-ku, Seoul, 121-110 (KR); Tae Gwan Park, #211-1501 Expo Apartment, Chunmin-dong, Yusong-ku, Taejon-si, 305-390 (KR); Yoon Sung Nam, #321-501 Zookong Apartment, Chamsil 3-dong, Songpa-ku, Seoul, 138-789 (KR)

( * ) Notice: Subject to any disclaimer, the term of this patent is extended or adjusted under 35 U.S.C. 154(b) by 674 days.

This patent is subject to a terminal disclaimer.

(21) Appl. No.: 10/423,536

(22) Filed: Apr. 25, 2003

(65) Prior Publication Data

US 2004/0013728 A1    Jan. 22, 2004

Related U.S. Application Data

(63) Continuation of application No. 09/700,380, filed as application No. PCT/KR99/00243 on May 14, 1999, now Pat. No. 6,589,548.

(30) Foreign Application Priority Data

May 16, 1998    (KR) ................................ 1998-17740

(51) Int. Cl.
    *A61K 9/14*    (2006.01)
    *A61K 9/16*    (2006.01)
    *A61K 9/50*    (2006.01)

(52) U.S. Cl. ...................... 424/489; 424/490; 424/499; 424/501

(58) Field of Classification Search ...................... None
See application file for complete search history.

(56) References Cited

U.S. PATENT DOCUMENTS 5,578,325 A * 11/1996 Domb et al. ................. 424/501
6,589,548 B1 * 7/2003 Oh et al. ..................... 424/426

OTHER PUBLICATIONS

R. Jeyanthi, et al. "Effect of solvent removal technique on the matrix characteristics of polylactide/glycolide microspheres for peptide delivery" Journal of Controlled Release 38 (1996) 235-244.
A. G. Shard, et al. "XPS and SSIMS Analysis Revealing Surface Segregation and Short-Range Order in Solid Films of Block Copolymers of PEO and PLGA" Macromolecules 1997, 30, 3051-3057.

* cited by examiner

*Primary Examiner*—S. Tran

(57) ABSTRACT

The present invention relates to the molecular sustained controlled release system constructed by the conjugation of molecules to be released with biodegradable polyester polymer via covalent bond and method for preparation thereof. In accordance with the present invention, the system may be formulated into microspheres, nanoparticles, or films. The molecular release rate from the above system can be regulated to be proportional to the chemical degradation rate of the biodegradable polyester polymers, resulting in near zero order kinetics profile of release without showing a burst effect. Moreover, the high loading efficiency of hydrophilic drugs can be achieved.

18 Claims, 15 Drawing Sheets

- ● PBS buffer pH 7.4, daily injection
- ○ DOX control (240 μg/kg body weight, daily injection)
- ▼ PLGA control
- ▽ PLGA-DOX conjugate (4.8mg/kg body weight)
- ■ Entrapped DOX in PLGA (2.4 mg/kg body weight)

CONTROLLED DRUG DELIVERY SYSTEM USING THE CONJUGATION OF DRUG TO BIODEGRADABLE POLYESTER

This application is a continuation of U.S. patent application Ser. No. 09/700,380 filed Nov. 14, 2000, now U.S. Pat. No. 6,589,548 which claims a benefit of priority from Korean Patent Application No. 1998/17740 filed May 16, 1998 through International Patent Application No. PCT/KR99/00243 filed May 14, 1999, the contents of each of which are incorporated herein by reference.

FIELD OF THE INVENTION

The present invention relates to the sustained controlled by the conjugation molecules with biodegradable polyester polymer, which may be formulated into microspheres, nanoparticles or films, and method for conjugation thereof. According to the system of this invention, drug release rate can be regulated to be proportional to the chemical degradation rate of the biodegradable polyester polymer, resulting in near zero order kinetic profile of release without showing a burst effect. Moreover, it is possible to achieve the high loading efficiency of hydrophilic drugs in the formulation into microspheres, nanoparticles, or films.

DESCRIPTION OF THE PRIOR ART

It is difficult to maintain constant drug concentration in blood through the established injection or oral administration. Therefore, in order to maintain constant drug concentration in blood, the methods that polymer carrier is slowly degraded have been studied for the release of drug in biodegradable polymer carrier at a constant rate [Langer, R., Chem. Eng. Commun., 6, 1–48 (1980); Langer, R. S. and Peppas, N. A., Biomaterials, 2, 201–214 (1981); Heller, J. CRC Crit., Rev. Ther. Drug Carrier Syst., 1(1) 39–90 (1984); Holland, s. J. Tighe, B. J. and Gould, P. L., J. Controlled Release, 155–180 (1986)]. Such a biodegradable polymer carrier system has an advantage that, since the polymer carrier is degraded into low molecules, the additional elimination process of the carrier is not needed.

Many kinds of biodegradable polymers have been used as carriers, in general, aliphatic polyester polymers have been frequently used, such as poly(lactic acid), poly(glycolic acid), poly(D-lactic-co-glycolic acid), poly(L-lactic-co-glycolic acid), poly(D,L-lactic-co-glycolic acid), poly(caprolactone), poly(valerolactone), poly(hydroxybutyrate) and poly(hydrovalerate), etc. [Peppas, L. B. International journal of pharmaceutics, 116, 1–9 (1995)]. In particular, poly(D-lactic-co-glycolic-acid), poly(L-lactic-co-glycolic acid), poly(D,L-lactic-co-glycolic acid) (hereinafter, generally referred to as poly(D/L-lactic-co-glycolic acid) have been widely used. It was ascribed that biodegradable polymers with various life span of degradation could be produced and drug release could be regulated for weeks or years, by controlling the molar composition ratio of monomer comprised of lactic acid and glycolic acid or controlling the molecular weight of the polymer.

However, the formulation comprising of drugs and aliphatic polyester polymers as carrier has some difficulties in controlling the rate of drug release over desired period due to an initial burst effect. This resulted from the fact that drug release is not dependent on the polymer erosion process but on the diffusion of drug. Particularly, this problem is serious for hydrophilic drug such as peptides or protein. For example, microspheres or films consisting of gentamycin sulfate and polyester polymer carrier were observed to show the initial burst effect. Also, it was reported that hydrophilic gentamycin compound had initial burst effects over 50% [Mauduit, J., Bukh, N., and Vert. M., J. Controlled release, 23, 209–220 (1993); Mauduit, J., Bukh, N., and Vert. M., J. Controlled release, 23, 221–230 (1993); Mauduit, J., Bukh, N., and Vert. M., J. Controlled release, 25, 43–49 (1993)] and neurotensin analog over 20% [Yamakawa I., Tsushima, Y., Machida, R., and Watanable, S., J. Pharma. Sci., 81, 808–811 (1992)]. To solve such a problem, there have been efforts to develop new methods for manufacturing various microspheres, nanoparticles and films [Peppas, L. B. International journal of pharmaceutics, 116, 1–9 (1995)].

Biodegradable, biocompatible matrices for drug delivery including microspheres, nanoparticles, and films have been widely used for an injectable depot formulation of various small molecular weight drugs, peptides, and proteins which required multiple administrations. It has been known that drug release kinetic rate from the microspheres, nanoparticles, and films is determined by diffusion and/or polymer erosion process [D. D. Lewis, et al, in Biodegradable Polymers as Drug Delivery System, in M. Chasin and R. Langer (Eds.), Marcel Dekker, New York (1990) pp. 1–41]. For small diameter microspheres and nanoparticles as an injectable dosage form, it has been difficult to predictably control the drug release kinetic rate over a desied period due to an initial burst effect combined with the process of relatively faster diffusion of the drug than the erosion of the matrices. This problem is particularly acute for hydrophilic drugs that are believed to exist in pre-formed microporous aqueous channels within the microspheres [S. Cohen, et al., Pharm. Res. 8 (1991) 173–720].

The most common method of preparing microspheres and nanoparticles for hydrophilic drugs is a double emulsion solvent evaporation technique which adopts a two phase emulsion system composed of polymer dissolved organic phase containing primary aqueous emulsion droplets as a dispersed phase and a continuous phase of water [Y. Ogawa, et al., Chem. Pharm. Bull. 36 (1998) 2576–2588]. This method inevitably generates porous morphology in the microspheres and nanoparticles matrices, leading to burst and very fast release kinetics of the hydrophilic drugs through pre-existing macro- and micro-pores. For hydrophobic drugs, a single oil-in-water emulsion system has been employed to prepare drug loaded microspheres and nanoparticles. In this case, drug release kinetic rate was mainly controlled initially by diffusion through existing pores and later by polymer erosion process, resulting in a triphasic release profile. Most of previous studies for controlled release of hydrophilic drug from biodegradable polyester microspheres and nanoparticles, however, could not achieve a zero order release profile over an extended period because of complicated nature of drug release mechanism, that is, a diffusion coupled polymer erosion process [H. T. Wang, et al., J. Controlled. Release 17 (1991) 23–32].

On the other hand, a new drug delivery system has been developed though conjugation synthetic polymer to drug via covalent bond or modifying the biodegradable polymer. For example, the system developed by conjugating drug with polyethylene glycol (hereinafter, referred to as PEG) approved by FDA, which is hydrophilic, linear, and non-immunologic polymer, was reported to increase circulation time of the drug in blood stream [Zhu, K. J., XiangZhou, L. and Shilin, Y. J. Appl. Polym. Sci. 39, 1–9 (1990; Davis, F.

F., Kazo, G. M., Nucci, M. L., and Abuchwski, A., In Lee, V. H. L. (Ed.), Peptide and Protein Drug Delivery, Dekker, New York, 831–864 (1991)). PEG has been applied to many drugs. At least more than six classes of PEG-enzyme complexes, including PEG-adenosine amylase, PEG-antigen, PEG-asparaginase, and PEG-uricase, are under the clinical trials or approved by FDA.

Recently, anti-cancer drugs have been chemically conjugated to various polymers for the purpose of their efficient passive targeting to solid tumors [R. Duncan, et al., *Anti-cancer drugs,* 3: 175–210 (1992), H. Maeda, et al., *J. Med. Chem,* 28: 455–461 (1985), T. Minko, et al., *J. Control Release,* 54: 223–233 (1998)]. The "enhanced permeation and retention (EPR)" effect on the site of tumor capillaries plays a critical role in accumulating the polymer conjugates in the solid tumors, while minimizing the glomerular excretion rate [H. Maeda., et al., *CRC Crit. Rev. Ther. Drug Carrier Sys.,* 6: 193–210 (1989), L. W. Seymour, et al., *CRC Crit. Rev. Ther. Drug Carrier Sys.,* 9: 132–187 (1992)]. Water soluble polymer conjugates based on poly(N-(2-hydroxypropyl)methacrylamide) have been extensively studied and are now under clinical trials [V. Omelyanenko, et al., *J. Control Release,* 53: 25–37 (1998)]. Another promising approach is to conjugate doxorubin to an amphiphilic block copolymer composed of polyethyleneglycol (PEG) and poly($\alpha,\beta$-aspartic acid), which leads to a polymeric micelle structure [M. Yokoyama, et al., *Bioconjugate Chem.* 3: 295–301 (1992)]. Besides the above two examples, doxorubicin has been physically adsorbed onto and/or encapsulated within nondegradable and biodegradable nanoparticles [J. Leroux, et al., Microencapsulation: Methods and Industrial Applications, S. Benita Ed., Marcel Dekker, New York, 535–576 (1996), P. Couvreur, et al., *J. Control. Rel.,* 17: 187–198 (1991)], protein nanoparticles [Y. Morimoto, et al., *Chem. Pharm. Bull.,* 29: 1433–1439 (1981)], and liposomes [A. A. Gabizon, et al., *Pharm. Res.,* 10: 703–708 (1993)., K. Yachi, et al., *Biopharm. Drug Dispos.,* 16: 653–667 (1995)]. The above doxorubicin formulations intend to achieve passive targeting of doxorubicin loaded particles to the tumor site.

The recent approach indicates that if the conjugation of drug with biodegradable polyester is applied to the formulation of nanoparticle, this technique will provide not only the aforementioned advantages such as high loading efficiency and zero order release kinetics but also the passive targeting of the anticancer drugs to solid tumor.

SUMMARY OF THE INVENTION

It accordance with the present invention, There is provided a novel sustained controlled release system constructed by, conjugation of molecules to be released with biodegradable polyester polymers.

In particular, the present invention provides a sustained controlling-release system with high loading efficiency of drug molecules.

The present invention also provides the sustained controlled release system formulated into microspheres, preferably about 1 to about 300 µm in diameter, nanoparticles, preferably about 50 to about 1000 nm in diameter, or films.

In addition, this invention Provides the sustained controlled release system using biodegradable polyester polymer selected from the groups comprising poly(lactic acid), poly(glycolic acid), poly(D-lactic-co-glycolic acid), poly(L-lactic-co-glycolic acid), poly(D,L-lactic-co-glycolic acid), poly(caprolactone), poly(valerolactone), poly(hydroxybutyrate), poly(hydrovalerate), polydioxnanone, and derivatives thereof. More preferably, the biodegradable polyester polymer is about 1,000 Da to about 100,000 Da in molecular weight.

This invention additionally provides the system using poly(lactic-co-glycolic acid) as a biodegradable polyester with various compositions, wherein the preferred ratio of lactic acid and glycolic acid, from 1:10 to 10:1.

This invention provides the system employing the ester bond, amide bond, anhydride bond, urea bond, urethane bond, carbonate bond, thioester bond, disulfide bond, imine bond, thioester bond, disulfide bond or carbamate bond for conjugation of molecules with biodegradable polyester polymers.

This invention also provides the system wherein the specified moieties are either directly bound to one another through covalent bond, or else indirectly bound to one another with an additional moiety such as a bridge, spacer, or linkage moieties.

Additionally, this invention provides the system wherein the molecules to be loaded are selected from the groups comprising peptides, proteins, therapeutic agents, diagnostic agent, and non-biological materials such as pesticides, herbicides, and fertilizers.

This invention also provides a process of preparing the sustained controlled release system, comprising the steps of;

1) activating drug molecule or polymer by mixing with coupling agents, bases, and, if needed, additives;
2) conjugating drug molecule with polymer by adding drug molecule to the activated polymer solution of step 1, or by adding polymer to the activated drug molecule solution of step 1;
3) purifying polymer-molecule conjugate of step 2.

Accordingly, an object of the present invention is to provide biodegradable polyester polymer-drug conjugates formed via covalent bond.

Another object of the present invention is to provide biodegradable polyester polymer-drug conjugates having an advantage that the removal process of the polymer carrier is not required after drug release, as a result of polymer degradation into low molecular weight molecules.

Still the object of the present invention is to provide microspheres, nanoparticles or films that are easy to formulate from biodegradable polyester polymer-drug conjugate by a single oil in water emulsion method.

Yet another object of the present invention is to provide microspheres, nanoparticles and films to get the high loading efficiency of hydrophilic drug.

A further object of the present invention is to provide a sustained controlled release system wherein the initial burst of molecules is prevented and zero order release profile is achieved by controlling the molecule release rate in accordance with the chemical degradation rate of the biodegradable polymer.

DETAILED DESCRIPTION OF THE INVENTION

Figure 1:
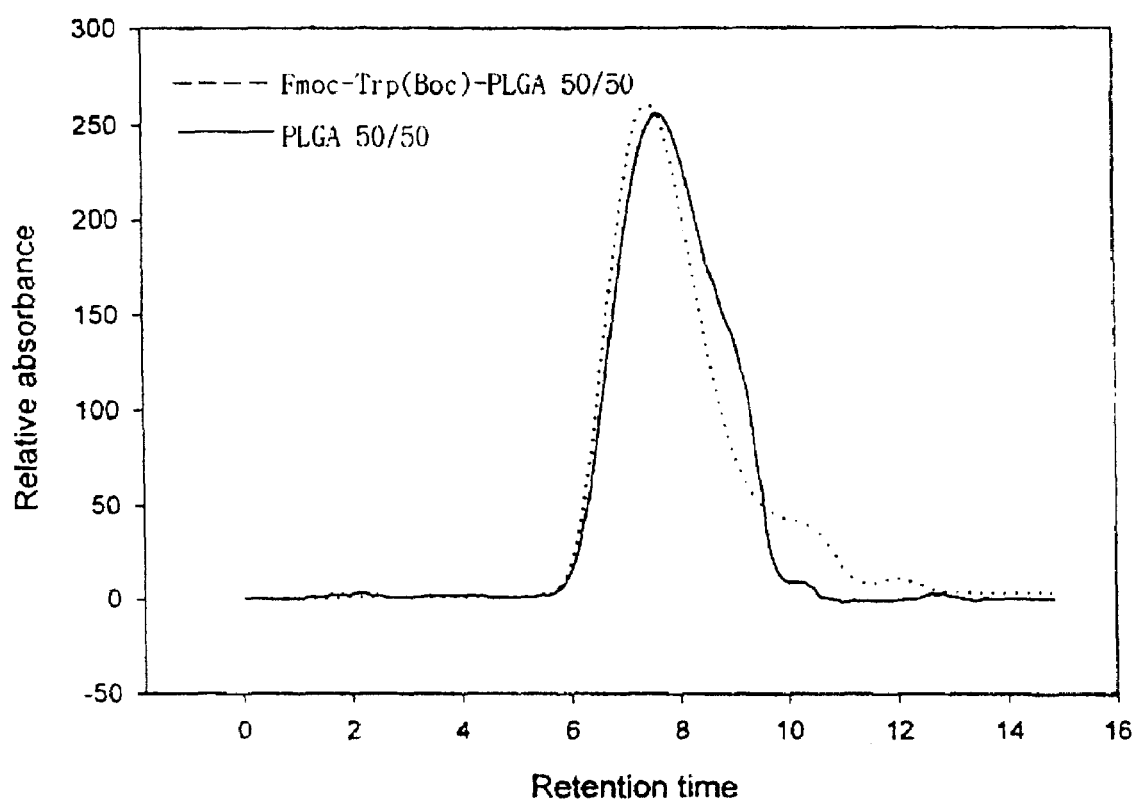
FIG. 1 shows Gel Permeation chromatogram profiles of PLGA 50/50 before conjugation monitored at 230 nm (solid line) and Fmoc-Trp(BOC)-PLGA 50/50 conjugate monitored at 267 nm (dotted line)

The present invention relates to a sustained controlled release system constructed by the conjugation of drug molecules to the terminal groups of biodegradable polyester polymers via covalent bond, with high loading efficiency.

The present invention also relates to the method for preparing system wherein the solvent is selected from the group comprising methylene chloride, N,N-dimethylformamide, dimethylsulfoxide, and tetrahydrofuran.

In accordance with the present invention, the conjugate of target molecules and polymers is formulated into microspheres and polymers is formulated into microspheres, nanoparticles, or films. In the preferred embodiments, microspheres are approximately 1 to approximately 300 μm and nanoparticles are about 50 to about 1,000 nm in size.

The present biodegradable polyester polymer may be selected from the group comprising poly(lactic acid), poly(glycolic acid), poly(D-lactic-co-glycolic acid), poly(L-lactic-co-glycolic acid), poly(D,L-lactic-co-glycolic acid), poly(caprolactone), poly(valerolatone), poly(hydroxybutyrate), poly(hydrovalerate), polydioxnanone, and their derivatives. Preferably, the molecular weight range of the biodegradable polyester polymer is from about 1,000 Da to 100,000 Da.

Also, the biodegradable polyester polymer is selected from poly(lactic-co-glycolic acid) with various compositions (the ratio of lactic acid and glycolic acid, from 1:10 to 10:1) for satisfying the required biocompatibility of the molecule to be delivered including degradation rate and degradation profile.

The present invention is based on the conjugation of molecule to be delivered with biodegradable polyester via covalent bond. Covalent bonding structure is defined as follows.

Biodegradable polyester polymer has two kind of functional group, i.e., carboxyl and hydroxy group. The conjugation method, therefore, may be divided into two groups; the method wherein the molecules are coupled to carboxyl group of polyester polymer, and the method wherein the molecules are coupled to hydroxy group of polyester polymer. Namely, drug molecules can be covalently conjugated with more than one functional group of polyester polymer. In either method, the drug-polymer conjugate may be formed by appropriate linker or spacer additionally, for coupling or introducing the multifunctional groups, respectively.

Moreover, preferably the covalent bond may be formed using multifunctional ligand. In particular, one or more drug molecules may be conjugated to the triglycerol covalently bound to biodegradable polyester polymer. In another preferred embodiment, covalent bond may be formed by conjugating alkyl spacer or other feasible spacer to glycerol or glyceraldehyde.

In case of all mentioned above, the covalent bond between molecules and biodegradable polyester polymers may be ester bond, amide bond, anhydride bond, carbonate bond, urea bond, urethane bond, thioester bond, disulfide bond, imine bond, or carbamate bond, which can or can not be broken down by enzymatic or nonenzymatic degradation.

Illustrative examples of molecules that can be used in the system of the present invention include; biologically active compounds such as peptides, proteins, therapeutic agents, diagnostic agents, and non-biological materials such as pesticides, herbicides, and fertilizers.

Preferably, peptides are selected from the group comprising insulin, calcitonin, ACTH, glucagon, somatostatin, somatotropin, somatomedin, parathyroid hormone, erythropoietin, hypo-thalmic releasing factors, prolactin, thyroid stimulating hormone, endorphins, enkephalins, vasopressin, non-naturally occurring opioids, superoxide dismutase, interferon, asparaginase, arginase, arginine deaminase, adenosine deaminase, ribonuclease, trypsin, chemotrypsin, and pepsin.

Therapeutic agent may comprise anticancer agents such as dideoxyinosine, floxuridine, 6-mercaptopurine, doxorubicin, daunorubicin, I-darubicin, cisplatin, methotrexate, etc.; antibiotics such as erythromycin, vancomycin, oleandomycin, ampicillin, etc.; anticoagulant such as heparin; germicides such as ara-A, acrylguanosine, nordeoxyguanosine, azidothymidine, dideoxyadenosine, dideoxythymidine, etc.; antiarrythmic agent; and prodrugs and derivatives thereof.

The present invention also relates to a method for manufacturing the sustained controlled release system.

A method, wherein the conjugation of molecule with polyester polymer is carried out, comprises the steps of;

1) activating drug molecule or polymer by mixing with coupling agents, bases, and, if needed, additives;
2) conjugating drug molecule with polymer by adding drug molecule to the activated polymer solution of step 1, or by adding polymer to the activated drug molecule solution of step 1;
3) purifying polymer-molecule conjugate of step 2.

The coupling agent of step 1 may be one or more selected from the group comprising bis(2-oxo-3-oxazolydinyl)phosphonic chloride (BOP-Cl), bromo-tris-pyrrolidino-phosphonium hexafluorophosphate (PyBroP), benzotriazol-1-yl-oxy-tris-pyrrolidino-phosphonium hexafluorophosphate (PyBOP), 2-(1H-benzotriazol-1-yl)-1,1,3,3-tetramethyluronium hexafluorophosphate (HBTU), dicyclohexyl carbodiimide, disuccinimidyl carbonate, 1-(3-dimethylaminopropyl)-3-ethylcarbodiimide (EDC), bis(2-oxo-3-oxazolydinyl) phosphin, diisopropyl carbodiimde (DIPC), 2-(1H-benzotrioxazolyl)-1,1,3,3-tetramethyl-uronium tetrafluoroborate (TBTU), 2-(5-norboren)-2,3-dicarboxy-imido)-1,1,3,3-tetramethyluronium tetrafluoroborate (TNTU), para-nitrophenylchloroformate and O-(N-succinimidyl)-1,1,3,3-tetramethyluronium tetrafluoroborate (TSTU).

The base of step 1 may be selected from the groups comprising triethylamine, N-methylmorpholine, pyridine, 1,8-diazabicyclo[5,4,0]-undec-7-ene, N,N-dimethyl aminopyridine, and N,N-diisopropyl ethylamine.

The additives of step 1 may be one or more selected from the groups comprising hydroxybenzotriazole, pentafluorophenol, and N-hydroxy-5-norboren-endo-2,3-dicarboximide.

In this invention, we designed microspheres, nanoparticles, and films by conjugating various target molecules to the terminal end groups of biodegradable polyester microspheres, nanoparticles, and films via a biodegradable ester bond, amide bond, or carbamate linkage to obtain a zero order release kinetic profile. The strategy is that when the conjugated biodegradable polyester chains are randomly hydrolyzed and water soluble fractions are leached out [R. A. Kenley, et al., *macromolecules*, 20 (1987) 2398–2403], target drug molecules which were bound to the terminal ends of the cleaved polyester oligomer are released out concomitantly. The drug release rate from the proposed system is expected to be proportional to mass erosion rate of the biodegradable microspheres, nanoparticles, and films. After the release, polyester oligomer chains conjugated to the drug moiety would be further degraded, eventually generating an intact free drug and/or drug with 1–3 polyester oligomer chain.

The main advantage of the conjugation of drug to biodegradable polyester is, first to prevent the initial burst and control the sustained release of molecules from microspheres, nanoparticles, and films. Second, drug-polymer conjugates are easily formulated into microspheres, nanoparticles, and films by a single Oil-in-Water emulsion method with very high encapsulation efficiency (almost 100%).

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Coupling Molecule to PLGA via Covalent Bond (1) Coupling Peptide to PLGA via Amide Bond Antifungal peptide (PCT-KR 96-0034, KYIVFVFK) filed by this applicant was synthesized by using automatic 431A peptide synthesizer (Biosystems) through solid phase synthesis, and then deprotected by trifluoroacetic acid solution. Purified product was obtained using reverse phase high performance liquid chromatography (HPLC).

After dissolving PLGA5010 (Mw 10,000, lactic acid: glycolic acid, 1:1 mole ratio) in mixed solvent including N,N-dimethylformamide and methylene chloride, the above peptide dissolved in a small dose of dimethylformamide was added. Coupling reagent of EDC/HOBt or DCC/HOBt and base of triethylamine were added, and this solution was stirred at room temperature for 12 hours. Reaction process was assayed, using thin layer chromatography and gel permeation chromatography (GPC).

After the reaction was completed, ether was added and the precipitate was dissolved in methylene chloride. This solution was washed with 2% hydrochloric acid or brine (saturated-NaCl solution). The organic phase was concentrated by using rotary evaporator and lyophilized.

The reaction forming covalent linkage was monitored by gel permeation chromatography, fluorescence analyzer and UV spectrophotometry.

(2) Coupling Lysozyme to PLGA via Amide Bond

PLGA and lysozyme were dissolved in dimethylsulfoxide (DMSO), followed by adding agents of DCC and HOBt and the solution was stirred ar room temperature. Diethyl ether was added to precipitate the product.

The progress of reaction was monitored by gel permeation chromatography and fluorescence analyzer.

Example 2

Coupling Molecule to Activated PLGA via Covalent Bond (1) Method for Activating PLGA: Synthesis of p-nitrophenyl Carbonate of PLGA p-nitrophenyl chloroformate was dissolved in dried methylene chloride, and then temperature was lowered to 0° C. PLGA5010 dissolved in dried methylene chloride was added to the above solution. Pyridine was added and stirred at 0° C. for 30 minutes, then further stirred at room temperature for 1~3 hours or stirred at 0° C. for 3~6 hours. Precipitate was formed with ether.

By precipitation using ether and methylene chloride, product was purified and characterized by gel permeation chromatography and UV spectrum.

(2) Coupling Antifungal Peptide with Activated PLGA

Antifungal peptide dissolved in dimethylformamide was slowly added to polymer solution of the above step 1.

Triethylamine was added to the solution and stirred at room temperature for 6~24 hours. Reaction process was monitored, using gel permeation chromatography, UV spectrum, and fluorescence analyzer.

After the reaction was completed, ether was added to remove dimethylformamide and the precipitate was dissolved in methylene chloride. This solution was washed with 2% hydrochloric acid or brine, and the organic phase was concentrated by rotary evaporator, and then lyophilized.

The conjugates were characterized by gel permeation chromatography, fluorescence analyzer, and UV spectrophotometry.

(3) Coupling Amphotericin B to Activated PLGA

Amphotericin B dissolved in dimethyl sulfoxide was slowly added to polymer solution of above step 1, and then stirred at room temperature for 6~24 hours. By gel permeation chromatography and thin layer chromatography, the reaction process was monitored.

After the completion of the reaction, ether was added to the solution, followed by centrifugation at 3,000 rpm for 15 minutes. The resulting precipitate was dissolved in methylene chloride and filtrated, and the filtrate was concentrated. After dissolving the filtrate in methylene chloride, it was washed with water. The organic phase was concentrated by rotary evaporator and dried.

(4) Coupling Doxorubicin with Activated PLGA

Poly(D,L-lactic-co-glycolic acid) having lactic/glycolic molar ratio of 50/50 was obtained from Wako Chemical (Japan) [PLGA5005]. The average molecular weight was 8,020 as determined from gel permeation chromatography. This polymer has free hydroxyl and carboxylic groups at its terminal ends. Doxorubicin and p-nitrophenyl chloroformate were obtained from Sigma. All other chemicals were analytical grade.

One gram of PLGA dissolved in 10 ml of methylene chloride was activated by 72 mg of p-nitrophenyl chloroformate by adding 47 mg of pyridine (PLGA/p-nitrophenyl chloroformate/pyridine stoichiometrc molar ratio: 1/2.8/4.8) in a dropwise manner into the solution at 0° C. The reaction was carried out for 3 hours at room temperature under nitrogen atmosphere. The reaction process was monitored by gel permeation chromatography (GPC) with dual UV detection at 230 nm and 260 nm for ester group in the PLGA backbone and p-nitrophenyl group in the activated PLGA end group, respectively. The resultant solution was diluted by methylene chloride and washed with 0.1% HCl and brine solution. The organic phase was separated, dried on sodium sulfate, and then dried under vacuum (yield: 80%). The activated PLGA (0.1 g) dissolved in 3 ml of dimethylformamide (DMF) was reacted with 6.3 mg of doxorubicin in the presence of 5 mg of triethylamine for 24 hrs at room temperature under nitrogen atmosphere (stoichiometric molar ratio of activated PLGA/doxorubicin/triethylamine: 1/0.8/4). The process of doxorubicin conjugation to activated PLGA was monitored by GPC by an UV-Vis dual wavelength at 230 nm and 480 nm which detected the fraction of PLGA and doxorubicin conjugated PLGA, respectively. The precipitated product by the addition of cold diethyl ether was filtered and dried. The yield of conjugation reaction was 58%. The extent of doxorubicin conjugation to PLGA was determined by dissolving the conjugate in dimethylsulfoxide (DMSO), and them its absorbance was measured at 480 nm. A series of doxorubicin with different concentrations in DMSO were used as calibration standards.

(5) Gel Permeation Chromatography (GPC) of Doxorubicin-PLGA Conjugates

Figure 7:
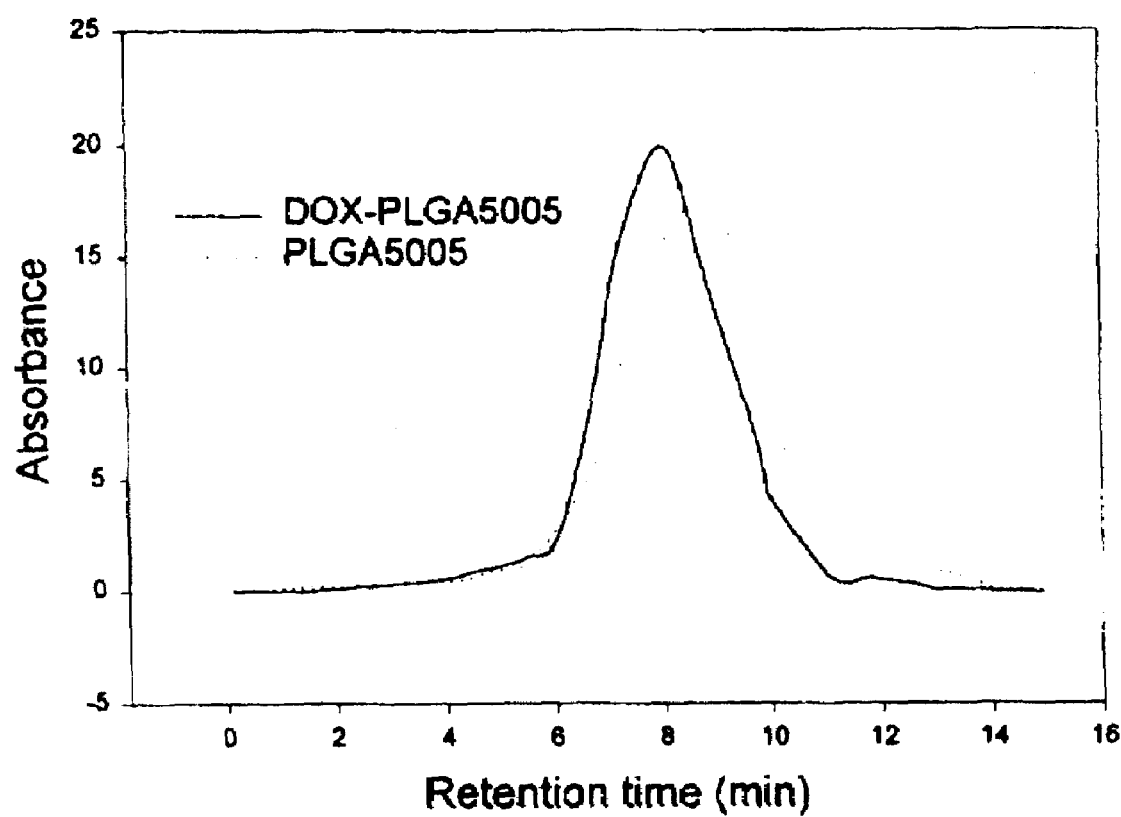
FIG. 7 shows Gel Permeation chromatogram of doxorubicin conjugated polymer (solid line) and unconjugated polymer (dotted line).

The synthesized conjugates were characterized by GPC using Gilson 306 pump with UV-Vis detector. The GPC column was Shodex K-803 (300×7.8 mm, Phenomenex, USA) and tetrahydrofuran was used as a mobile phase with a flow rate of 1 ml/min. Molecular weight of the conjugate was calculated using a series of polystyrene standards (Mr: 114,200, 44,000, 13,700, and 3,700). The PLGA-doxorubicin conjugate was analyzed by gel permeation chromatography as shown in FIG. 7. The conjugated PLGA was eluted earlier than the unconjugated PLGA, supporting that doxorubicin was conjugated to PLGA. Average molecular weight of the conjugate was 9,210 and that of PLGA was 8,020, respectively. The slight increase in molecular weight was due to the doxorubicin conjugation and the removal of low molecular weight PLGA fraction in the process of purification of doxorubicin-PLGA conjugate. From the GPC profile, it was confirmed that free doxorubicin was completely removed from the synthesized PLGA-doxorubicin conjugate.

Example 3

Coupling Activated Molecule to PLGA via Covalent Bond

Coupling Fmoc-Trp(Boc) to PLGA via Ester Bond (1) Coupling Reaction of Fmoc(Boc) to PLGA Various coupling reagents and reaction conditions were studied in the conjugation of various molecules into polyester polymer. First, different coupling reactions were explored by employing various coupling agents for poly(D, L-lactic-co-glycolic acid) (PLGA) 50/50 to maximize the conjugation yield. Poly(D,L-lactic-co-glycolic acid) (lactic acid/glycilic acid ratio, 75/25 and 50/50) were purchased from Wako Pure Chemical Industries Ltd. (PLGA 5010 and 7510). The two PLGA polymers with 75/25 and 50/50 lactic/glycolic monomer composition ratios had molecular weight (Mw) of 9,800 and 8,700, respectively, as determined by gel permeation chromatography. The PLGA polymer used in this reaction had an uncapped free carboxylic acid group at one terminal end and a hydroxyl group at the other end. Typically, Fmoc-Trp(Boc) (80 mg, $1.5 \times 10^{-4}$ mole) dissolved in $CH_2Cl_2$ (3 ml) under nitrogen atmosphere was mixed with various combinations of coupling reagents ($1.5 \times 10^{-4}$ mole) and bases ($1.5 \times 10^{-4}$ mole). PLGA with lactic/glycolic acid 50/50 ratio (0.43 g, $5 \times 10^{-5}$ mole) dissolved in 7 ml of $CH_2Cl_2$ was then added to the solution. The coupling reaction was carried out at room temperature for 4~6 hrs. The resulting solution was diluted with the addition of 20 ml $CH_2Cl_2$ and washed with brine. An organic layer was separated, concentrated, and dried under vacuum. The conjugated Fmoc-Trp(Boc)-PLGA was further purified by the following precipitation procedure. The product mixture dissolved in 2 ml $CH_2Cl_2$ was precipitated by the addition of 30 ml diethyl ether. This precipitation was repeated three times. The separation of unconjugated free Fmoc-Trp(Boc) from a mixture of Fmoc-Trp(Boc)-PLGA conjugate and unreacted PLGA was confirmed by gel permeation chromatography (GPC). The conjugate was lyophilized and stored at −20° C. until use. Coupling reagents, 2-(1H-benzotriazol-1-yl)-1,1,3,3,-tetramethyluronium hexafluorophosphate (HBTU), N-hydroxybenzotriazole (HOBt), benzotriazol-1-yl-oxy-tris-pyrrolidino-phosphonium hexafluorophosphate (PyBOP), and bromo-tris-pyrrolidino-phosphonium hexafluorophosphate (PyBroP) were obtained from Novabiochem.

Bis(2-oxo-3-oxazolidinyl)-phosphonic chloride (BOP-Cl) was purchased from Advanced Chemtech. 1-(3-dimethylaminopropyl)-3-ethylcarbodiimide (EDC), tetrahydrofuran (THF), methylene chloride (anhydrous), diethyl ether (anhydrous), triethylamine (TEA), polyvinylalcohol. (PVA, 88% hydrolyzed, Mw 25,000) and 4-dimethylaminopyridine (DMAP) were obtained from Aldrich. All other reagents were analytical grade and used without further purification.

TABLE 1

Synthesis of Fmoc-Trp(Boc)-PLGA (50/50)

| Mole ratio of PLGA:Fmoc-Trp(Boc) | Coupling reagent | Base or additive | Reaction time | Conjugation percent |
|---|---|---|---|---|
| 1:3 | BOP-Cl | TEA | 4 h | No reaction |
| 1:10 | BOP-Cl | TEA | 6 h | <10% |
| 1:3 | EDC | HOBt | 4 h | <10% |
| 1:3 | EDC | HOBt | 6 h | <10% |
| 1:3 | PyBOP | TEA | 4 h | 37% |
| 1:3 | HBTU | TEA. | 4 h | 20% |
| 1:3 | PyBroP | TEA | 4 h | 60% |
| 1:3 | PyBroP | TEA | 6 h | 63% |
| 1:3 | PyBroP | DMAP | 4 h | 63% |

As seen in Table 1, various coupling agents and bases in different combinations were used to provide Fmoc-Trp(Boc)-PLGA conjugate in different yield. The conjugation percent was mainly dependent on the kind of coupling agents. Among the reaction conditions tested, PyBroP/TEA combination resulted in the greatest conjugation percent of 63% in PLGA 50/50. Thus, the PyBroP/TEA combination was also used for the conjugation of PLGA 75/25. The conjugation percent of Fmoc-Trp(Boc) to PLGA 75/25 was 46%. FIG. 1 shows GPC profiles of PLGA 50/50 and Fmoc-Trp(Boc)-PLGA 50/50 conjugate. It can be seen that the conjugate was eluted slightly earlier than the unconjugated PLGA due to the additional presence of Fmoc-Trp(Boc) group in one end terminal of PLGA chain. It should be mentioned that the elution peak of the conjugate monitored at 267 nm does not reflect a fraction of unconjugated PLGA that was not detected at that wavelength. Elemental analysis data (calculated C 47.3%, H 4.73%, N 0.19%, and O 47.8%; measured C 47.0%, H 4.6%, N 0.2%, and O 48.2%) support the conjugation percent of 63%.

(2) Characterization of Fmoc-Trp(Boc)-PLGA

The conjugates were characterized by GPC using Gilson 306 pump with UV detector. The GPC column was Shodex K-803 (300×7.8 mm, Phenomenex) and THF was used as a mobile phase with a flow rate of 1 ml/min. The eluted conjugate was monitored by UV at dual wavelengths (230 nm for PLGA and 267 nm for Fmoc group). Average molecular weight of the conjugate was calculated using a series of polystyrene standards (Mr: 114,200, 44,000, 13,700, and 3,700). The conjugation was confirmed by measuring fluorescence of Fmoc-Trp(Boc)-PLGA (excitation at 295 nm and emission at 355 nm for Trp group and excitation at 260 nm and emission at 305 nm for Fmoc group). The conjugation percent of Fmoc-Trp(Boc) to PLGA was determined by measuring absorbance of Fmoc-Trp(Boc)-PLGA in THF at 267 nm using a series of Fmoc-Trp(Boc) with a different concentrations as standards. The conjugation percent was calculated as a relative molar ratio of Fmoc-Trp(Boc) conjugated PLGA compared to the total PLGA amount in the sample.

Coupling Doxorubicin to PLGA via Ester Bond (1) Preparation of Fmoc-Doxorubicin

Dox HCl salt (50 mg, 86 μmole) was dissolved in N,N-dimethylformamide (DMF) (2 ml), and Fmoc-Osu (30 mg, 90 μmole) was added, followed by adding 30 μl (172 μmole) of N,N-diisopropylethylamine. After 3 h, the solvent was evaporated in vacuo, and residue was crystallized by trituration from 0.1% aqueous trifluoroacetic acid (TFA) (vol/vol). The crystals were collected by filtration and washed once with cold diethyl ether to remove the trace of excess Fmoc-Osu. After freeze drying, 55 mg of 98% pure N-Fmoc-Dox was obtained (84% yield).

(2) Conjugation of Fmoc-Dox and PLGA5005

PLGA5005 (0.18 g) and Fmoc-Dox (20 mg) were dissolved in $CH_2Cl_2$ (10 ml). PyBroP (15.6 mg), triethylamine (TEA) (20 μl), and dimethylaminopyridine (DMAP) (4.5 mg) were added to stirred solution under nitrogen. After 15 hrs, reaction mixture was diluted with $CH_2Cl_2$ (20 ml). Organic layer was washed with 5% aqueous HCl solution (×2) and brine (×2). Organic layer was concentrated under vacuum. Conjugation between Fmoc-Dox and PLGA was monitored by GPC and UV-Vis detector (480 nm for Dox, 267 nm for Fmoc, 230 nm for PLGA).

(3) Deprotection of Fmoc Group in Fmoc-Dox-PLGA Conjugate

Fmoc-Dox-PLGA conjugate was dissolved in DMF (3 ml) and 300 μl of piperidine was added. After 5 min, the reaction mixture was placed in an ice bath and acidified by the addition of a mixture containing a 300 μl of TFA, 700 μl of pyridine, and 2 ml of DMF. The solvent was evaporated in vacuo. The residue was solidified by trituration from the addition of diethyl ether in DMF. The solids were dissolved in $CH_2Cl_2$ (30 ml) and washed with 5% HCl aqueous solution and brine. Organic layer was concentrated under vacuum. The solid was purified by the precipitation method using diethyl ether.

Example 4

Preparation and Characterization of Mocrosphere with the Conjugate Fmoc-Trp(Boc) to PLGA (1) Mocrosphere Preparation PLGA microspheres containing Fmoc-Trp(Boc)-PLGA conjugates were prepared by an oil-in-water (O/W) single emulsion technique. Four different formulations were prepared as listed in Table 2. One hundred mg of Fmoc-Trp(Boc)-PLGA conjugates [PLGA 50/50 (formulation A), a 50:50 mixture of PLGA 50/50 and 75/25 (formulation B), and PLGA 75/25 (formulation C)] and 400 mg of PLGA 50/50 were dissolved in a co-solvent mixture of 2.5 ml of DMSO and 2.5 ml of methylene chloride., As control microspheres (formulation D), 10 mg of free Fmoc-Trp(Boc) and 490 mg of PLGA 50/50 were used for the formulation. The resulting solutions were emulsified in 500 ml of 0.3% (w/v) PVA/phosphate buffered saline (PBS) solution for 20 min by homogenization at 6,000 rpm using a PowerGen 700 (Fisher Scientific) and subsequently stirred magnetically for 3 hrs at room temperature to extract DMSO and evaporate methylene chloride. The hardened microspheres were collected by centrifugation at 8,000 rpm for 20 min, washed twice with deionized water, and then lyophilized.

TABLE 2

Formulation of Microspheres

| Formulation | PLGA 50/50 Weight (mg) | Fmoc-Trp (Boc)-PLGA, Weight (mg) | Encapsulation Efficiency, % | Average Size (μm) |
|---|---|---|---|---|
| A | 400 | 100[a] | 100 | 8.76 (1.2) |
| B | 400 | 100[b] | 100 | 8.33 (0.9) |
| C | 400 | 100[c] | 100 | 8.52 (1.7) |
| D | 490 | 10[d] | 20.1 | 8.62 (1.6) |

[a]Fmoc-Trp(Boc)-PLGA 50/50 conjugate
[b]Fmoc-Trp(Boc)-PLGA 75/25 conjugate
[c]A 1:1 mixture of Fmoc-Trp(Boc)-PLGA 50/50 conjugate and Fmoc-Trp (Boc)-PLGA 75/25 conjugate
[d]Free Fmoc-Trp(Boc)

The Fmoc-Trp(Boc)-PLGA conjugates with different copolymer compositions of 50/50 and 75/25 mixed with PLGA 50/50 was formulated into microspheres using a single oil-in-water emulsion method as shown in Table 2. The microspheres (formulations A, B, and C) containing the Fmoc-Trp(Boc)-PLGA conjugates exhibit almost 100% encapsulation efficiencies owing to their limited solubility in water, whereas conventionally prepared microspheres (formulation D) encapsulated with unconjugated Fmoc-Trp (Boc) show only 20.1% encapsulation efficiency due to the diffusion of moderately water soluble Fmoc-Trp(Boc) into the aqueous phase during the solvent evaporation procedure.

(2) Scanning Electron Microscopy and Particle Size Distribution

Microsphere shape and surface morphology were estimated using a scanning electron microscopy (SEM, Philips 535M). Freeze-dried microspheres were mounted on an aluminum stub covered with a carbon adhesive tape and then coated with gold. Size average and distribution of microspheres were determined by a Coulter Counter (CASY™, Scharfe System, Germany). Microspheres suspended in isotonic saline solution were forced to flow through a capillary. The resistance change by a particle was electronically scaled and counted. SEM pictures indicate spherical shaped microspheres having a very smooth surface morphology. There were no apparent discrepancies in morphologies between conjugated and unconjugated Fmoc-Trp(Boc) containing microspheres. All the microspheres have their average size in diameter between 8.33 and 8.76 m.

Example 5

Fmoc-Trp(Boc)-OH and its Polyester Oligomer Release from Polymer Microsphere (1) In Vitro Release Study One hundred mg of freeze-dried microspheres were suspended in 30 ml of 0.033 M PBS (phosphate buffer saline) at pH 7.0 containing 0.01% sodium azide. They were incubated in a polypropylene tube at 37° C. under static condition. At predetermined intervals, the supernatant from each tube was collected by centrifugation at 8,000 rpm for 30 min and replaced with an equal volume of fresh buffer medium. The supernatant was frozen and stored at −20° C. until analyzed.

(2) Determination of Fmoc-Trp(Boc) Concentration in Release Medium

The Fmoc-Trp(Boc) concentration in the release medium was determined by measuring fluorescence intensity with a spectrofluorometer (RF-5301PC, Shimadzu, Japan) with an excitation at 295 nm and an emission at 314 nm. A standard calibration curve was constructed by dissolving 10 mg of free Fmoc-Trp(Boc) in 2 ml of acetonitrile and diluting it with excessive PBS buffer solution (pH 8). For the evaluation of cumulative release percent, the microspheres after incubation for 31 days were freeze-dried and the amount of unreleased Fmoc-Trp(Boc) in the microspheres was determined. Ten mg of dry microspheres dissolved in 1 ml of 0.1 N NaOH solution was incubation at 37° C. for 2 days. The remaining amount of Fmoc-Trp(Boc) was then determined. Osmolarity build-up in the release media was measured by a freezing point osmometer (model A0300, Knauser, Germany).

(3) Identification of Released Products from Microsphere Containing Fmoc-Trp(Boc)-PLGA Conjugates Released products from the microspheres encapsulated with Fmoc-Trp(Boc)-PLGA conjugate and free Fmoc-Trp (Boc) were separated by a $C_{18}$ reversed phase column by high performance liquid chromatography (HPLC) and the elution was monitored by fluorescence (excitation 260 nm, emission 305 nm). The released Fmoc-Trp(Boc)-PLGA oligomer conjugates were further incubated in 0.033 M sodium phosphate buffer (pH 9) at 37° C. for additional 3 days to see whether authentic free molecule of Fmoc-Trp(Boc) was regenerated. This was performed by fractional separation of the conjugates in HPLC followed by taking its mass spectrum. The mass spectrometer (Platform II, Micromass, UK) was operated in a positive ion mode.

(4) Degradation Study

Figure 2:
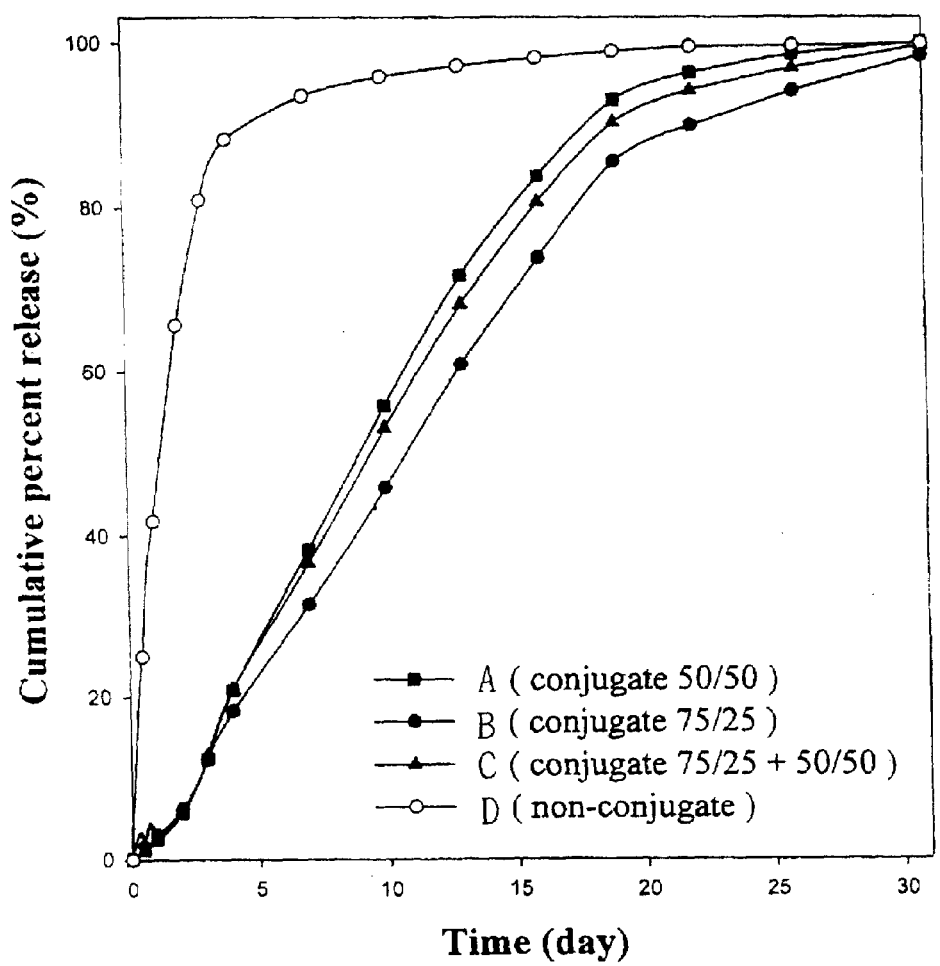
FIG. 2 shows release profiles of water soluble Fmoc-Trp (BOC)-PLGA oligomer conjugates in the medium as expressed in cumulative release percent.

FIG. 2 shows release profiles of Fmoc-Trp(Boc)-PLGA oligomer conjugates in the incubation medium from various microsphere formulations. It can be seen that the microspheres conjugated with Fmoc-Trp(Boc) exhibited constant release profiles over 20 days with an initial, short lag time period. On the other hand, the microspheres containing unconjugated Fmoc-Trp(Boc) showed a rapid release in the initial incubation stage, resulting in the early termination of release within 5 days. The microspheres (formulation A) containing Fmoc-Trp(Boc) conjugated with relatively fast degrading PLGA 50/50 polymer released their degradation products, Fmoc-Trp(Boc)-PLGA oligomer conjugates, faster than those (formulation B) conjugated with slowly degrading PLGA 75/25. Although their release rates did not differ greatly due to the relative small incorporation percentage of the conjugates in microspheres, this finding reveals that release kinetic rates of the drug conjugated with PLGA, indeed, can be judiciously controlled by appropriately selecting various PLGA polymers that degrade in different rates. Therefore, molecular weight and/or copolymer composition of PLGA to be conjugated would be an important variable to control the release rate in the present system. The formulation C having a 50:50 blend mixture composition of PLGA 50/50 and PLGA 75/25 in the Fmoc-Trp(Boc) conjugation demonstrates an intermediate release kinetic rate between the two release rates of formulation A and B, supporting our hypothesis that the chemical degradation rate of conjugated PLGA chains modulates the liberation rate of water soluble Fmoc-Trp(Boc)-PLGA oligomer fraction into the incubation medium as mentioned earlier.

Figure 3:
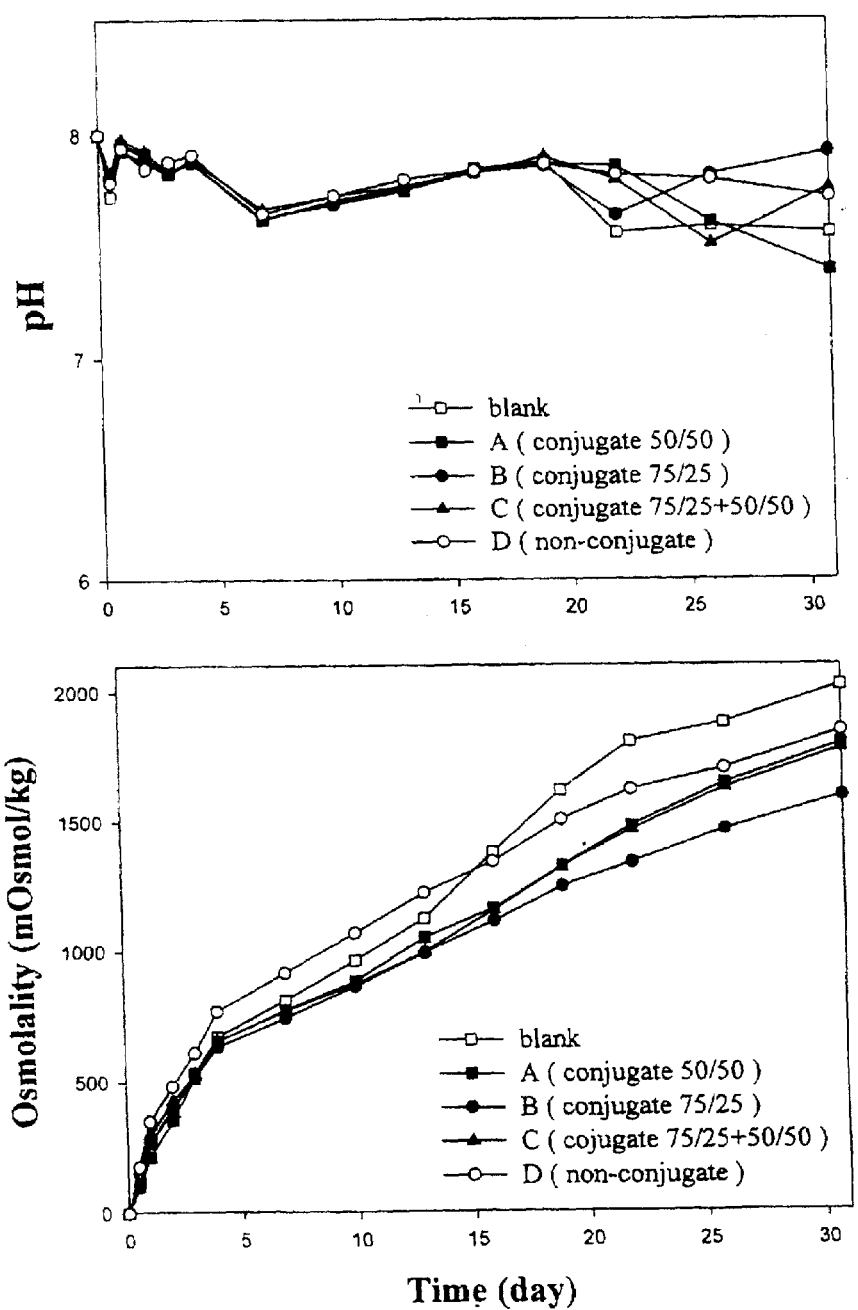
FIG. 3 shows pH (top) and osmolarity (bottom) change in the release medium as a function of incubation time.

FIG. 3 shows pH and cumulative osmolarity changes in the incubation medium as a function of time. Since the incubation medium was completely replaced by fresh buffer solution at every sampling period, there were insignificant pH variations during the release period, while the continuous build-up of osmolarity by the accumulation of water soluble PLGA degradation products in the medium was observed. This suggests that the release of degradation products from the PLGA 50/50 microspheres is a linear function of time [G. Crotts, et al., *J. Controlled Release*, 47 (1997) 101–111]. Initially increased osmolarity upon incubation can be attributed to the preferential diffusion of pre-existing small molecular weight PLGA oligomer fragments generated during the microsphere formulation process.

Figure 4A:
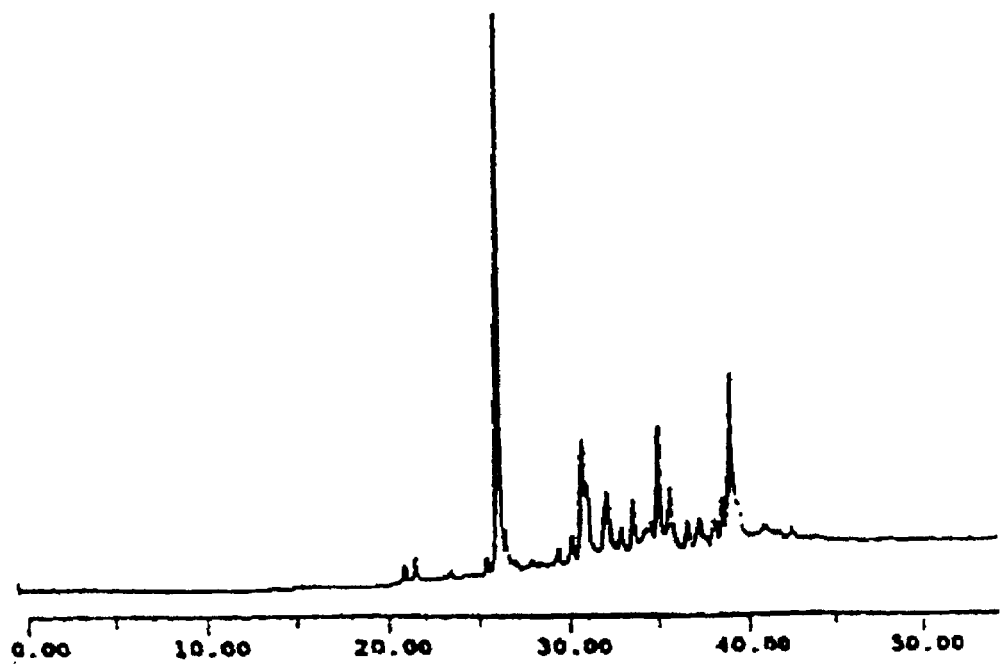
FIG. 4a shows the reversed phase HPLC chromatogram of released Fmoc-Trp(BOC)-PLGA conjugates from the formulation A of microspheres in Table 2 at day 7.
Figure 4B:
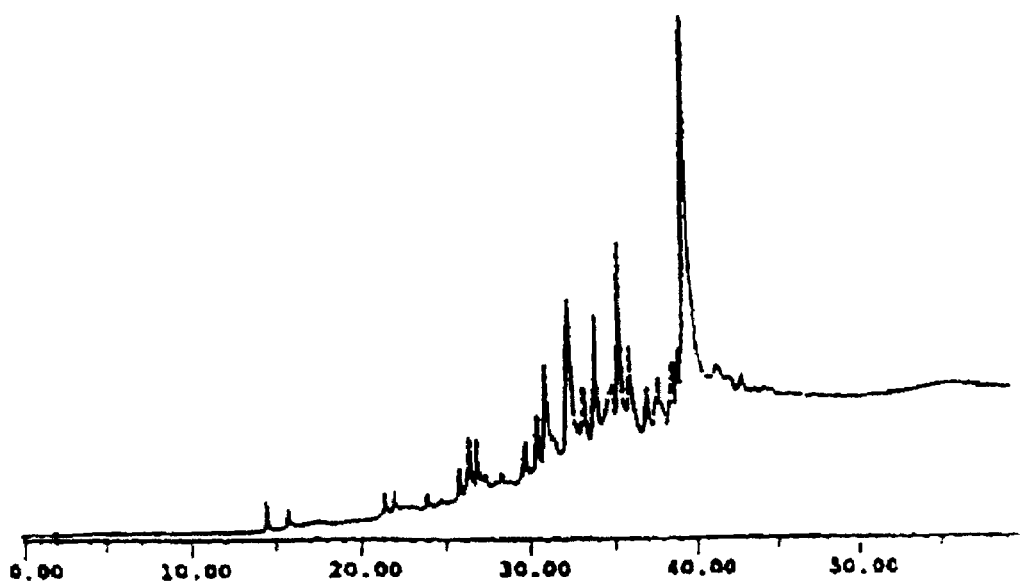
FIG. 4b show the reversed phase HPLC chromatogram of further degraded products of the released Fmoc-Trp(BOC)-PLGA conjugates described in FIG. 4a at pH 9 for 3 day incubation. Note that the elution peak appearing at 39.5 min is authentic Fmoc-Trp(BOC).
Figure 5A:
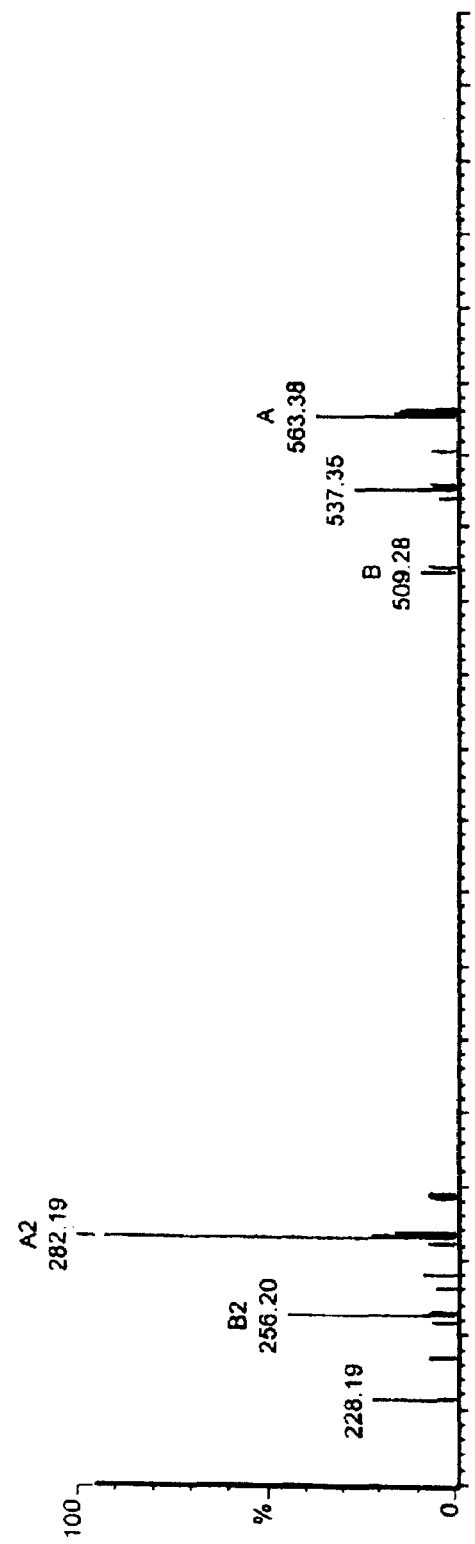
FIG. 5a shows mass spectra of hydrolyzed products obtained from Fmoc-Trp(BOC)-PLGA oligomer conjugates released in the incubation medium.
Figure 5B:
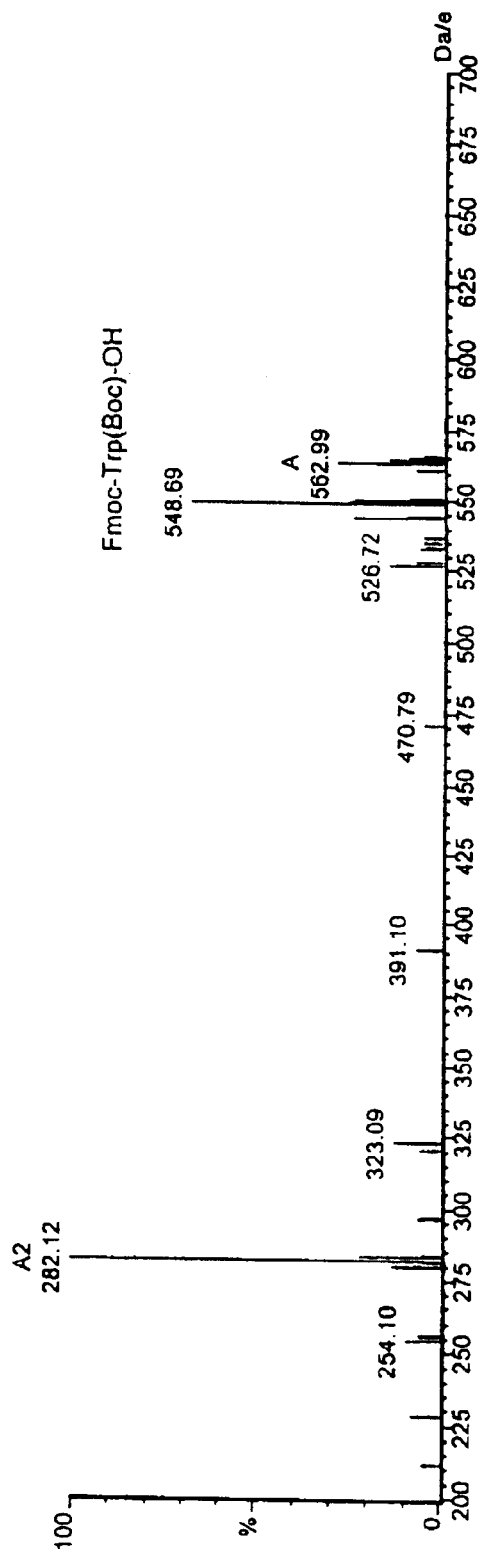
FIG. 5b shows mass spectra of authentic Fmoc-Trp (BOC).

FIG. 4 shows the reversed phase HPLC results obtained from the released Fmoc-Trp(Boc)-PLGA conjugates in the medium from the formulation A microspheres at day 7. The released conjugates are expected to have a mixture of molecular species composed of Fmoc-Trp(Boc) linked with different chain lengths of water soluble PLGA oligomers resulting from the random cleavage of PLGA chain. The HPLC result, however, demonstrates that the released Fmoc-Trp(Boc)-PLGA oligomer conjugates in the buffer medium were eluted earlier as a major single peak than the authentic Fmoc-Trp(Boc), although many other small unidentified peaks followed can also be seen. Further incubation of the released Fmoc-Trp(Boc)-PLGA oligomer conjugates in the buffer medium permitted the regeneration of intact Fmoc-Trp(Boc) peak as a result of chain scission of PLGA oligomers attached to Fmoc-Trp(Boc). This was additionally confirmed by mass spectroscopy. As shown in FIG. 5, the major product, from the additional incubation of the released Fmoc-Trp(Boc)-PLGA oligomers was identified as Fmoc-Trp(Boc) by its mass spectrum which shows $[M+K]^+$ and $[M+H+K]^{2+}$ ion peak at m/z=563.38 (calculated 565) and m/z=282.19 (calculated 283). Comparison of mass spectrum relative to that of intact Fmoc-Trp(Boc) incubates that the major components released from the microspheres were Fmoc-Trp(Boc)-PLGA oligomer conjugates and intact molecule of Fmoc-Trp(Boc) could be regenerated by further degradation.

Figure 6:
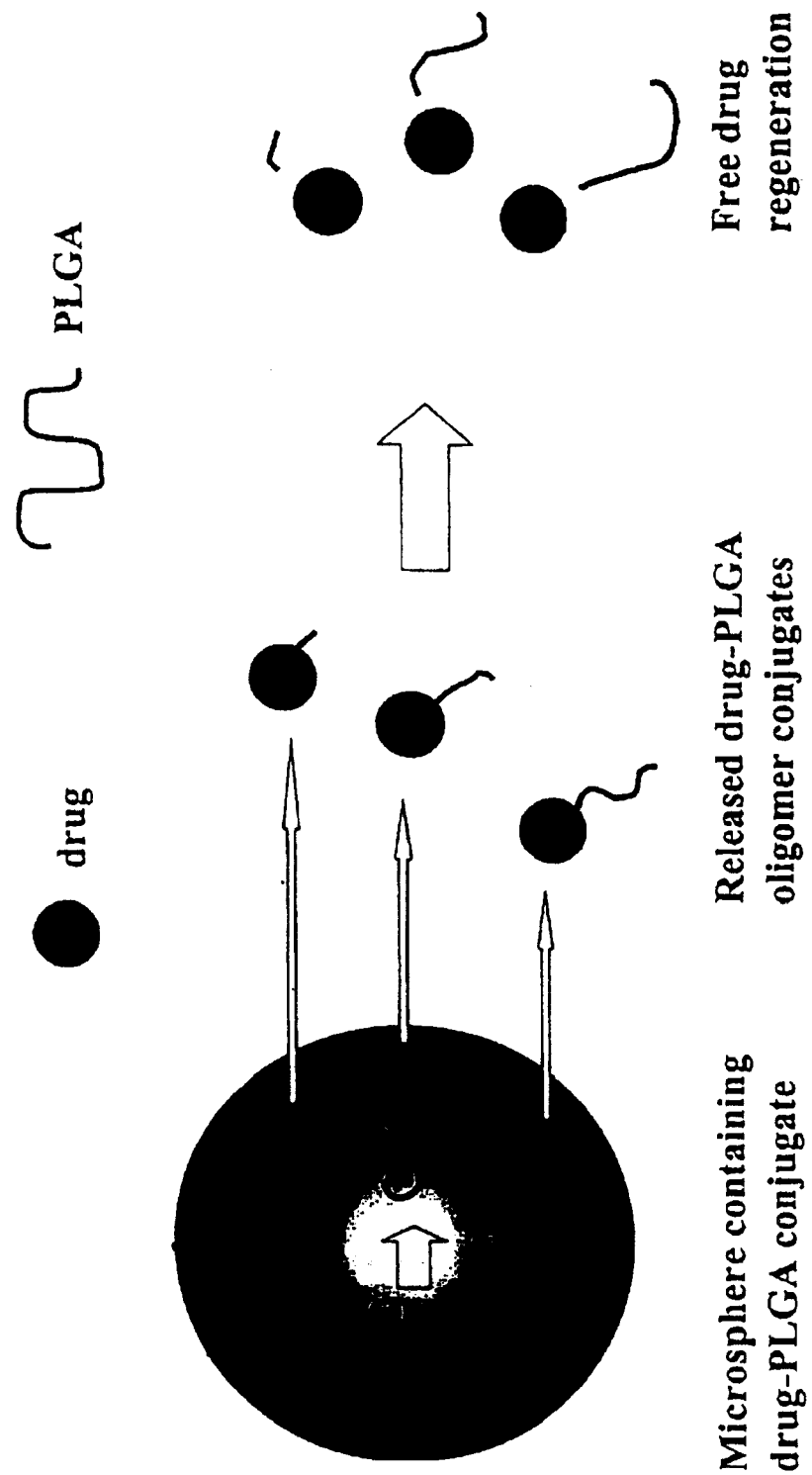
FIG. 6 shows the schematic illustration of drug-PLGA conjugation system.

It has been demonstrated that drug molecules could be delivered in a zero order fashion from biodegradable microspheres in a desired time span by the conjugation approach of a drug to PLGA chain end via an ester linkage. A schematic illustration of the proposed drug-PLGA conjugate system is depicted in FIG. 6. This strategy can be potentially applied to a wide range of hydrophilic drugs like antibiotics to improve their therapeutic effectiveness which require an extended duration of release at the injection site in vivo.

Example 6

Figure 8A:
FIG. 8 shows transmission electron microscopic pictures of nanoparticles containing doxorubicin-PLGA conjugate. Scale bars in A and B are 2 μm and 200 nm, respectively.
Figure 8B:
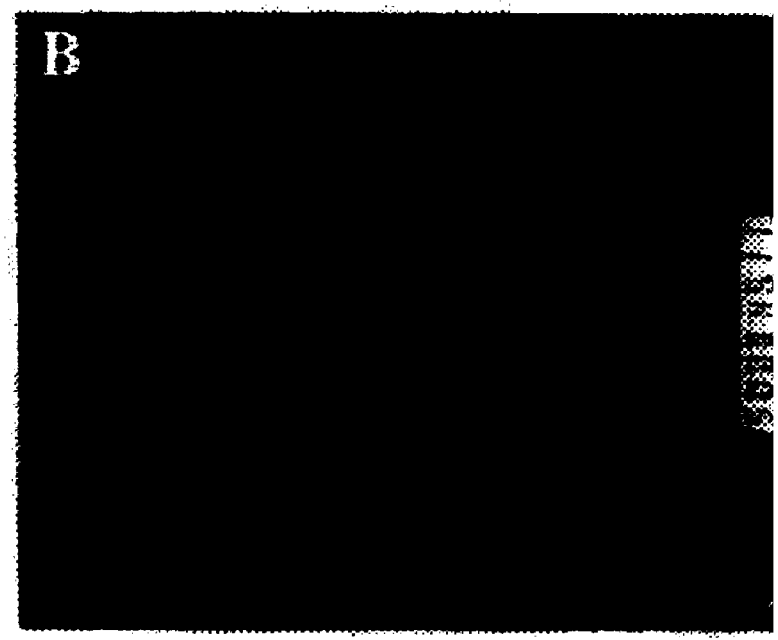

Preparation and Characterization of Nanoparticle with the Conjugate of Doxorubicin and PLGA via Carbamate Bond Two types of nanoparticles containing doxorubicin-PLGA conjugate and free doxorubicin were prepared by a spontaneous emulsion solvent diffusion method. One hundred mg PLGA-doxorubicin conjugate dissolved in 10 ml of acetone was slowly added to 100 ml of deionized water containing 1% (w/v) Pluronic F-127 under vigorous stirring condition. For the encapsulation of free doxorubicin into nanoparticles, 95 mg of PLGA and 5 mg of doxorubicin were co-dissolved in acetone and then used. The nanoparticles formed in the aqueous solution were collected by ultracentrifugation (Beckman, USA) at 15,000 rpm for 1 hr and resuspended in phosphate buffered saline (PBS) solution. The resuspended nanoparticles were stored under frozen condition (−20° C.) until use. The loading amount of doxorubicin within nanoparticles was determined by a spectroscopic method. A known amount of freeze dried nanoparticles was completely dissolved in dimethylsulfoxide (DMSO) and then the absorbance was measured at 480 nm according to the aforementioned method. Encapsulation efficiency was calculated based on the percent ratio of the amount of doxorubicin incorporated into nanoparticles to the initial amount used. Size distribution was measured by using a laser light scattering technique (ZetaPlus, Brookhaven Instrument Corp., USA). Transmission electron microscopy (TEM) picture was taken without a heavy metal staining procedure (CM20 Microscopy TEM, Philips) FIG. 8 shows transmission electron microscopy (TEM) picture of doxorubicin-PLGA conjugate encapsulated nanoparticles prepared by the spontaneous emulsion solvent diffusion method. The nanoparticles were unaggregated while maintaining an individual spherical shape. Average diameter and zeta potential of nanoparticles, as determined by a laser scattering method, was 269.7 nm and −58.1 mV for the free doxorubicin encapsulated nanoparticles, and 356.0 nm and −86.6 mV for the doxorubicin-PLGA conjugate encapsulated nanoparticles, respectively. The loading percent of free doxorubicin within nanoparticles was 0.26% (w/w) with 6.7% of loading efficiency. On the other hand, the doxorubicin-PLGA conjugate nanoparticles had 3.45% (w/w) loading percent with 96.6% efficiency. The remarkably enhanced loading percent as well as its concomitantly improved efficiency for the nanoparticles containing the conjugate were clearly due to the fact that the doxorubicin-PLGA conjugate became water insoluble while free doxorubicin was moderately water soluble.

Example 7

Characterization of Release Molecule from Nanoparticle with the Conjugate of Doxorubicin and PLGA via Carbamate Bond (1) Release Experiment Twenty mg of nanoparticles suspended in 20 ml of PBS buffer was sealed in a dialysis bag (M.W. cutoff: 10,000, Spectrapor). The dialysis bag was incubated in 30 ml of PBS buffer at 37° C. The released doxorubicin in the incubation medium was collected at predetermined time intervals and stored frozen for quantitative analysis. The release amount was analyzed at 480 nm.

(2) Reversed Phase High Performance Liquid Chromatography (HPLC)

The release doxorubicin and its PLGA oligomer conjugates in the medium was analyzed by a HPLC system (Waters 486) with detection at 480 nm, using the following operation conditions; PRP-3 column (4.1 mm×150 mm, Hamilton) as a reversed phase column, a linear gradient elution of water/acetonitrile from 95/5 to 50/50; a mobile phase flow rate of 1 ml/min.

(3) Degradation Study

Figure 9:
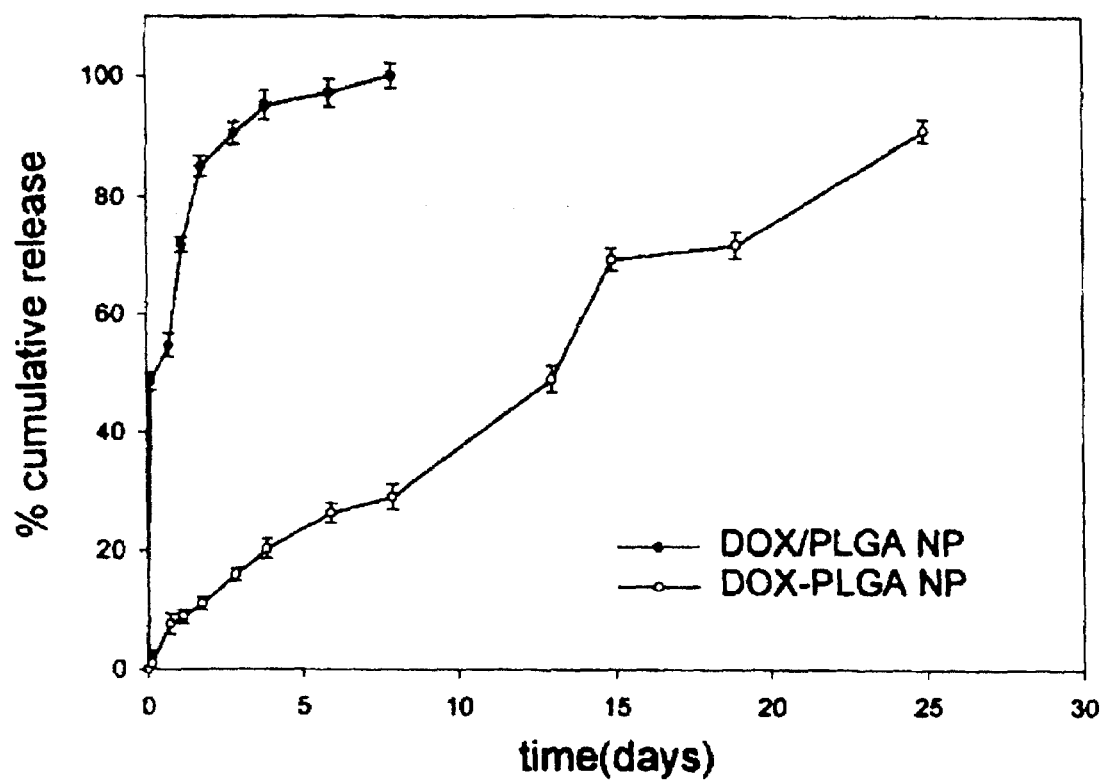
FIG. 9 shows release profile of doxorubicin from nanoparticles encapsulated with free doxorubicin (closed circle) and doxorubicin-PLGA oligomer conjugates from nanoparticles encapsulated with conjugated doxorubicin (open circle). Each data point was obtained from triplicate experiments.
Figure 10A:
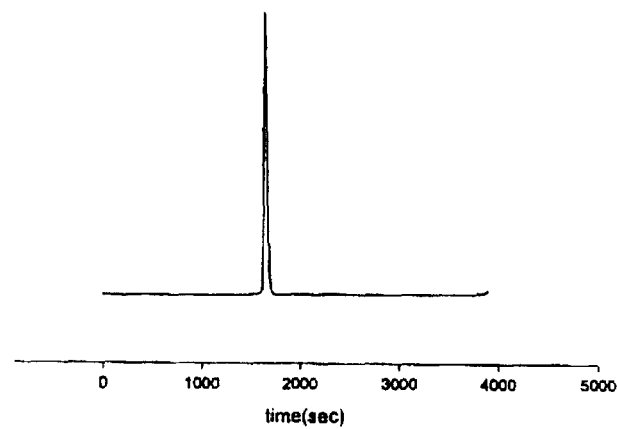
FIG. 10a shows the reversed phase HPLC result of free doxorubicin.
Figure 10B:
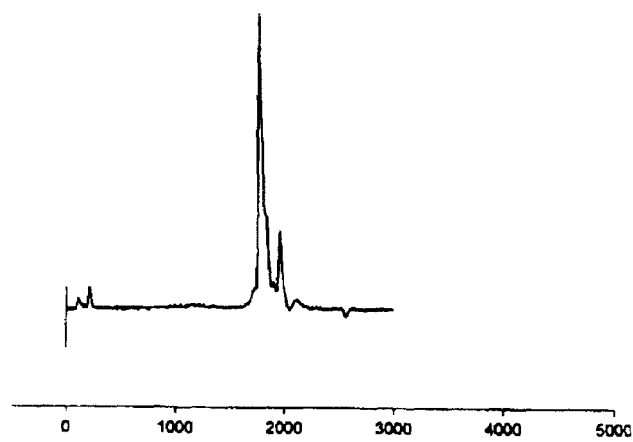
FIG. 10b shows the reversed phase HPLC result of the released fraction from nanoparticles encapsulated with conjugated doxorubicin for 19 days at 37° C.
Figure 10C:
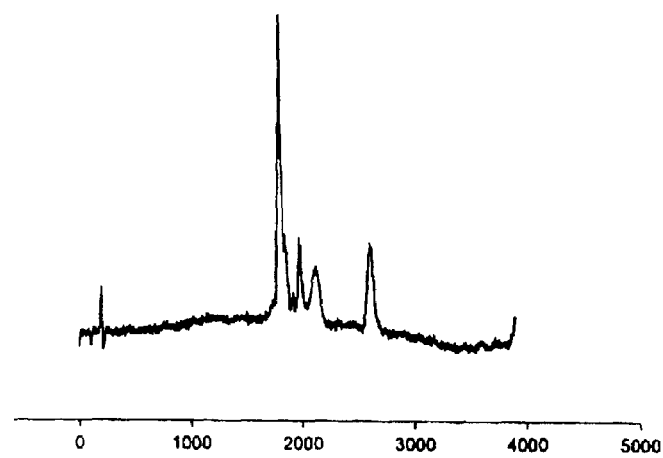
FIG. 10C shows the reversed phase HPLC result of the further incubation of the released fraction described in FIG. 10b for additional 4 days at 37° C.

Release profiles of doxorubicin from the two nanoparticles were compared as shown in FIG. 9. The release profile of the free doxorubicin encapsulated nanoparticles exhibits a very rapid release of doxorubicin in the early incubation stage, whereas that from the conjugate encapsulated nanoparticles shows a sustained release behavior over an extended period. It should be noted that the nanoparticles containing the doxorubicin-PLGA conjugate released a mixture species of doxorubicin-PLGA oligomer conjugates because the carbamate linkage between doxorubicin and PLGA was not easily cleaved in the aqueous medium. The sustained release action was caused by the gradual chemical degradation of conjugated PLGA backbone and subsequent controlled liberation of water soluble doxorubicin-PLGA oligomer conjugates in the incubation medium. Their release rate was solely dependent on how fast the conjugated PLGA chains were hydrolyzed to reach the critical Mw. The released fraction from the nanoparticles collected for 19 days incubation was subjected to reversed phase HPLC analysis as shown in FIG. 10. The released fraction contained a major peak and other eluting small peak, which were likely to be a mixture of water soluble doxorubicin-PLGA oligomer conjugates. The ester linkage adjacent to glycolic acid unit in the PLGA chain is more susceptible to hydrolysis than that to lactic acid unit, resulting in the production of non-randomly cleaved PLGA oligomer species enriched with lactic acid. Further incubation of the released fraction at 37° C. for 3 additional days resulted in the growth of the major peak with concomitant disappearance of the other small peaks. This suggests that the conjugated PLGA oligomers further degraded until one or two lactyl or glycolic monomer unit be still conjugated to doxorubicin via a stable carbamate linkage.

(4) In Vivo Cytotoxicity Assay

Cytotoxicities of doxorubicin and its PLGA oligomer conjugates released from nanoparticles were determined against human hepatoblastoma cell line (HepG2) obtained from Korea Research Institute of Bioscience and Biotechnology. Free doxorubicin and the released fraction from nanoparticles for 19 days incubation were used for determining the inhibition of cell growth using a tetrazolium dye (MTT) assay according to the previously established method [R. I. Freshney, Measurement of Viability and Cytotoxicity, Chapter 19 in *Culture of Animal Cells*, Third Edition., Wiley-Liss Inc., New York, 1994, pp. 287–307]. Dulbecco's modification of Eagle's MEM (DMEM) was used as a major cell growth medium and a humidified atmosphere (5% $CO_2$) was maintained for cell culture. HepG2 cells harvested in a logarithmic growth phase were seeded on 96 wells at a cell density of $5 \times 10^3$ cells/ml. After incubating the cells in a logarithmic phase with various concentrations of free doxorubicin and the released fraction for 72 hrs, the MTT assay was performed and the percentage of cell viability was then determined.

Figure 11:
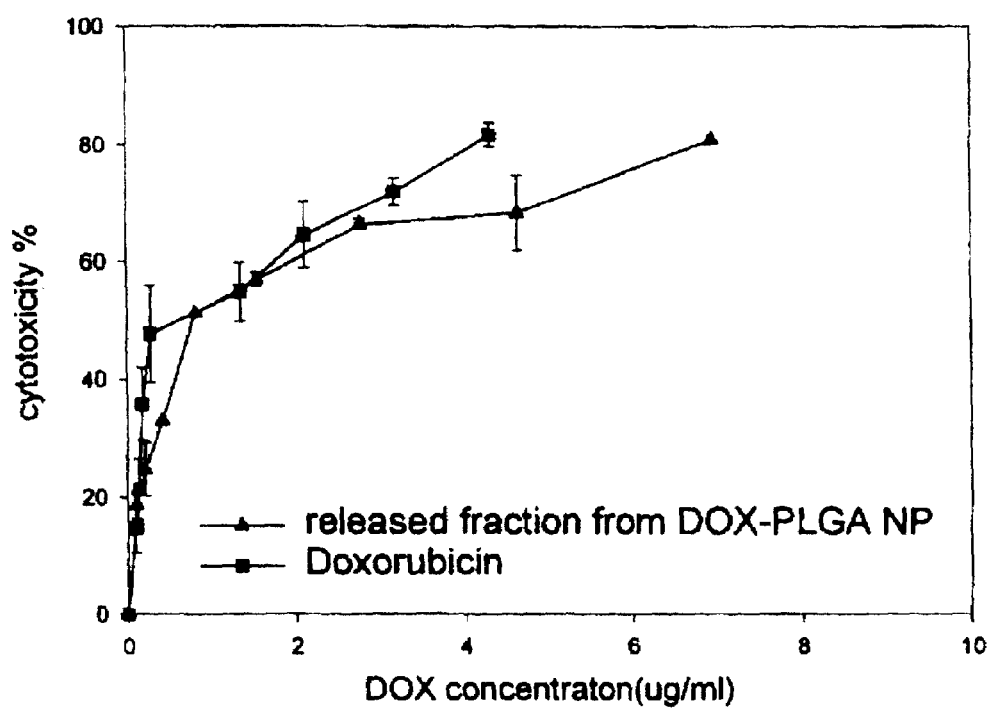
FIG. 11 shows cytotoxic activity of free doxorubicin (closed square) and the released fraction from nanoparticles containing conjugated doxorubicin (closed triangle) against HepG2 cells. Each data point was obtained from triplicate experiments.

The released fraction from the nanoparticles was tested whether a mixture of doxorubicin-PLGA oligomer conjugates still retained anti-cancer drug activity. FIG. 11 shows HepG2 cell viabilities against the released fraction from nanoparticles and free doxorubicin used as a positive control. It can be seen that the overall cytotoxic effect of the released fraction was slightly lower than that of free doxorubicin, presumably due to the presence of uncleaved PLGA oligomers conjugated to doxorubicin. The $IC_{50}$ value of the released fraction was 13.7 µM and that of free doxorubicin was 8.9 µM. In the literature, the reported $IC_{50}$ value of free doxorubicin was 7.3 µM [E. B. Yang, et al., *Cancer Letter*, 117: 93–98 (1997)]. Since a mixture of doxorubicin-PLGA oligomer conjugates might have different cytotoxic activities depending on the chain length of uncleaved PLGA conjugated to doxorubicin, the above value should be regarded as an average cytotoxic activiity for the realeased fraction during the study period.

Example 8

Characterization of Released Molecule from Nanoparticles with the Conjugate of Doxorubicin and PLGA via an Ester Bond (1) Release Experiment Twenty mg of nanoparticles suspended in 20 ml of PBS buffer was sealed in a dialysis bag (M.W. cutoff: 10,000, Spectrapor). The dialysis bag was incubated in 30 ml of PBS buffer at 37° C. The released doxorubicin in the incubation medium was collected at predetermined time intervals and stored frozen for quantitative analysis. The release amount was analyzed at 480 nm.

(2) Degradation Study

Figure 12:
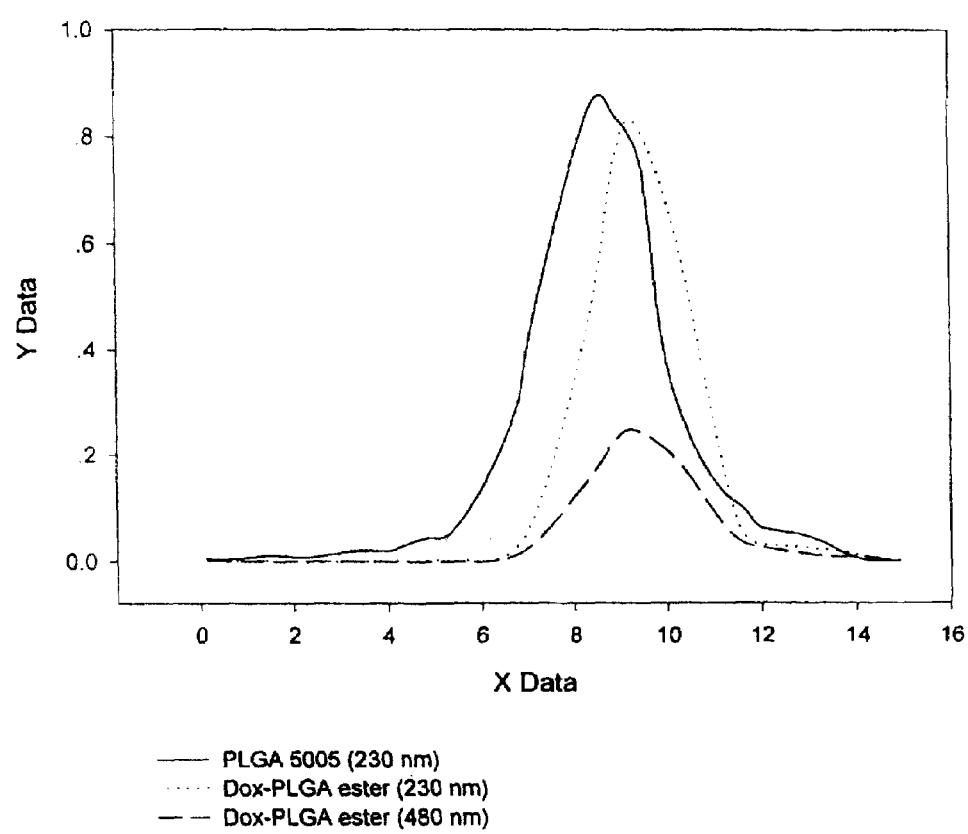
FIG. 12 shows Gel Permeation chromatogram of doxorubicin-PLGA conjugate via an ester bond.

FIG. 12 shows GPC profile of PLGA and its conjugated with doxorubicin via an ester bond. It can be seen that chemically conjugated PLGA has the absorbance at 480 nm, the characteristic wavelength of doxorubicin but free PLGA did not, which confirmed the success of the conjugation of doxorubicin with PLGA in chemically conjugated PLGA.

Figure 13:
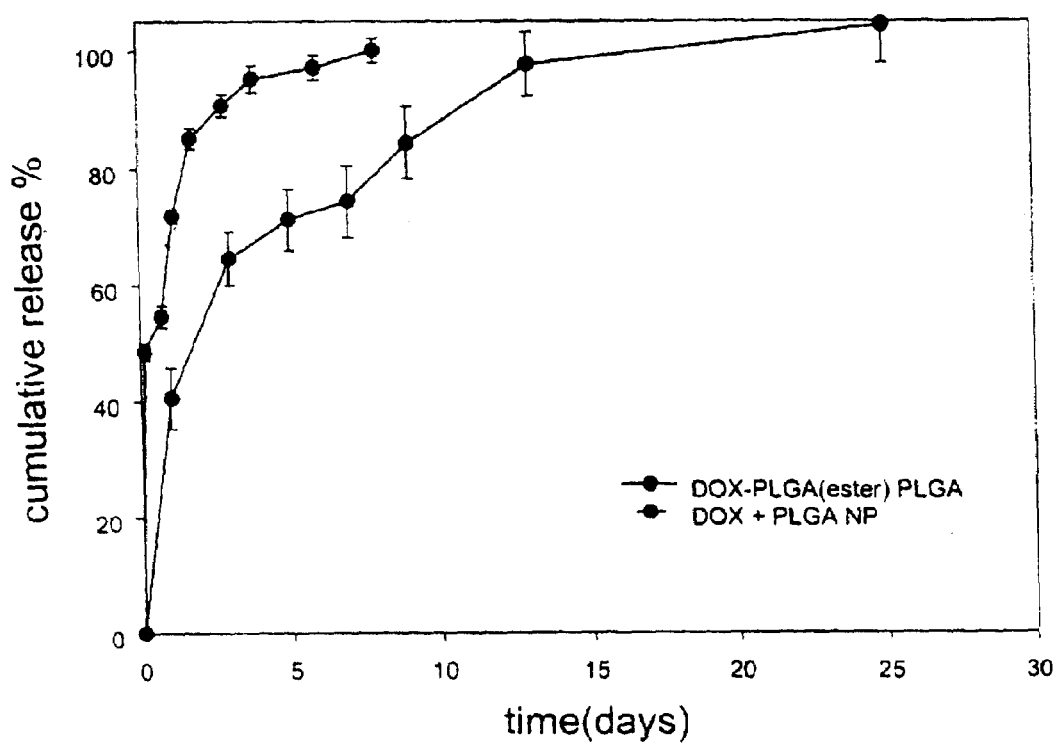
FIG. 13 shows release profiles of doxorubicin from nanoparticles encapsulated with free doxorubicin and doxorubicin-PLGA oligomer conjugates from nanoparticles encapsulated with conjugated doxorubicin via an ester bond.

Release profiles of doxorubicin from the two nanoparticles were compared as shown in FIG. 13. The release profile of the free doxorubicin encapsulated nanoparticles exhibits a very rapid release of doxorubicin in the early incubation stage, whereas that of doxorubicin chemically conjugated nanoparticles showed the comparatively slow release of doxorubicin and its PLGA oligomer in the early incubation stage. Theoretically, the release profile of doxorubicin chemically conjugated nanoparticles was expected to exhibit sustained release kinetic in the entire stage because the release was mainly controlled by mass erosion rate of the polymer. However, in this case, the molecular weight of biodegradable PLGA conjugated with doxorubicin was much lower than that of PLGA encapsulating doxorubicin because the harsh deprotection step of Fmoc-Doxorubicin hydrolyzed the polymer resulting in the preparation of low molecular weight of PLGA conjugated with Doxorubicin. Considering the low Mw of conjugated polymer, the initial release of doxorubicin was due to the high solubility of low mlecular weight of PLGA and its hydrolyzed oligomer in early incubation stage.

(3) In Vivo Antitumor Activity Assay

Antitumor activity against solid tumor of free doxorubicin, free PLGA, doxorubicin encapsulated in nanoparticles and doxorubicin conjugated with nanoparticles was evaluated with mouse EL4 thymoma cells. EL4 Cells ($2 \times 10^4$ cells in 0.1 ml of PBS pH 7.4 buffer) were transplanted into C57BL16 female mice (10 weeks old) subcutaneously on day 0 and drug injection started on day 10, when tumor diameter reached approximately 2 mm.

The mice were divided into five different groups, each group consisting of 6 mice. The first group, control group, was s.c. injected 100 µl PBS pH 7.4 daily during 12 days and the second group free doxorubicin (240 µg/kg body weight). However, the third group was s.c. injected placebo microsphere daily in the first two days, the fourth group nanoparticle conjugated with doxorubicin (2.4 mg/kg body weight) and the fifth group, doxorubicin encapsulated in nanoparticle (1.2 mg/kg body weight).

Figure 14:
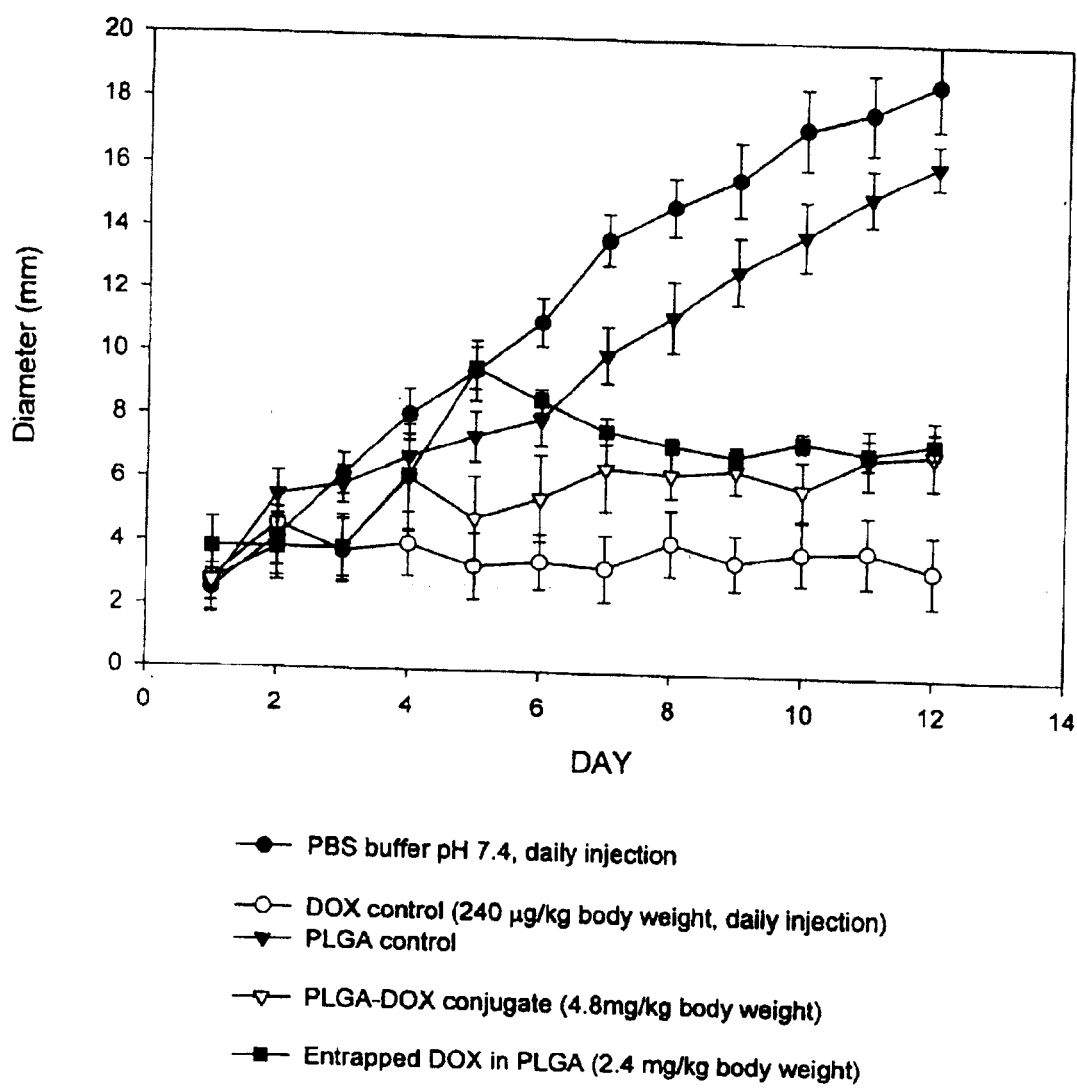
FIG. 14 shows in vivo antitumor activity against EL4 cell line of doxorubicin and its polymer nanoparticles.

FIG. 14 shows in vivo antitumor activity against EL4 cell line. Tumor diameter from the day of the first injection is plotted as the function of the day after injection of drug and its PLGA formulation. Daily injection of the free doxorubicin (240 μg/kg) during 12 days showed the significant tumor growth inhibition whereas daily injection of PBS buffer (pH 7.4) did not show any inhibition. Also no anti-tumor effect was observed for the mice group injected placebo PLGA nanoparticles. Antitumor effect was observed for two mice groups injected nanoparticles physically entrapping doxorubicin and chemically conjugated with doxorubicin. Interestingly, just daily injection of nanoparticle chemically conjugated with doxorubicin in the first two days shows a little better antitumor activity than that of doxorubicin physically entrapped nanoparticle and a comparable antitumor activity to the daily injection of free doxorubicin in 12 days.

What is claimed is:

1. A sustained controlled release system consisting of a drug molecule to be released directly conjugated to a biodegradable polyester polymer via a covalent bond, wherein the conjugation is carried out after activating the biodegradable polyester polymer by mixing with coupling agents, bases and optionally additives, wherein the coupling agents are selected from the group comprising bis(2-oxo-3-oxazolydinyl)phosphonic chloride (BOP-Cl), bromo-tris-pyrrolidino-phosphonium hexafluorophosphate (PyBroP), benzotriazol-1-yl-oxy-tris-pyrrolidino-phosphonium hexafluorophosphate (PyBOP), 2-(1H-benzotriazol-1-yl)-1,1,3,3-tetramethyl-uronium hexafluorophosphate (HBTU), dicyclohexyl carbodiimide, disuccinimidyl carbonate, 1-(3-dimethylaminopropyl)-3-ethylcarbodiimide (EDC), bis(2-oxo-3-oxazolydinyl)phosphin, diisopropyl carbodiimde (DIPC), 2-(1H-benzotrioxazolyl)-1,1,3,3-tetramethyl-uronium tetrafluoroborate (TBTU), 2-(5-norboren)-2,3-dicarboxyimido)-1,1,3,3-tetramethyluronium tetrafluoroborate (TNTU), para-nitrophenylchloroformate, and O-(N-succinimidyl)-1,1,3,3-tetramethyluronium tetrafluoroborate (TSTU), and wherein the bases are selected from the group consisting of triethylamine, N-methylmorpholine, pyridine, 1,8-diazabicyclo[5,4,0]-undec-7-ene, N,N-dimethyl aminopyridine, and N,N-diisopropyl ethylamine.

2. The system of claim 1, wherein the conjugate of the drug molecule with the biodegradable polyester polymer is formulated into microspheres, nanoparticles, or films.

3. The system of claim 2, wherein the microspheres are about 1 to about 300 μm in size.

4. The system of claim 2, wherein the nanoparticles are about 50 to about 1000 nm in size.

5. The system of claim 1, wherein, the biodegradable polyester polymer is selected from the group consisting of poly(lactic acid), poly(glycolic acid), poly(D-lactic-co-glycolic acid), poly(L-lactic-co-glycolic acid), poly(D,L-lactic-co-glycolic acid), poly(caprolactone), poly(valerolactone), poly(hydroxybutyrate), poly(hydrovalerate), polydioxnanone, and their derivatives.

6. The system of claim 1, wherein the biodegradable polyester polymer has a molecular weight from about 1000 Da to about 100000 Da.

7. The system of claim 1, wherein the biodegradable polyester polymer is a poly(lactic-co-glycolic acid) with the ratio of lactic acid and glycolic acid ranging from 1:10 to 10:1.

8. The system of claim 1, wherein the conjugate of the drug molecule with the biodegradable polyester polymer is employed via ester bond, amide bond, anhydride bond, carbonate bond, imine bond, thioester bond, urea bond, urethane bond, disulfide bond, or carbamate bond.

9. The system of claim 1, wherein the drug molecule is a biologically active compound selected from the group consisting of peptides, proteins, therapeutic agents, diagnostic agents, and non-biological materials.

10. The system of claim 9, wherein the peptides are selected from the group consisting of insulin, calcitonin, ACTH, glucagon, somatostatin, somatotropin, somatomedin, parathyroid hormone, erythropoietin, hypo-thalmic releasing factors, prolactin, thyroid stimulating hormone, endorphins, enkephalins, vasopressin, non-naturally occurring opioids, superoxide dismutase, interferon, asparaginase, arginase, arginine deaminase, adenosine deaminase, ribonuclease, trypsin, chemotrypsin, and pepsin.

11. The system of claim 9, wherein the therapeutic agents comprise anticancer agents selected from the group consisting of dideoxyinosine, floxuridine, 6-mercaptopurine, doxorubicin, daunorubicin, I-darubicin, cisplatin, methotrexate, prodrugs thereof, and derivatives thereof.

12. The system of claim 9, wherein the therapeutic agents comprise antibiotics selected from the group consisting of erythromycin, vancomycin, oleandomycin, ampicillin, prodrugs thereof, and derivatives thereof.

13. The system of claim 9, wherein the therapeutic agents are anticoagulant, prodrugs thereof, or derivatives thereof.

14. The system of claim 13, wherein the anticoagulant is heparin.

15. The system of claim 9, wherein the therapeutic agents comprise germicides selected from the group consisting of ara-A, acrylguanosine, nordeoxyguanosine, azidothymidine, dideoxyadenosine, dideoxythymidine, prodrugs thereof, and derivatives thereof.

16. The system of claim 9, wherein the therapeutic agents are antiarrhythmic agent, prodrugs thereof, or derivatives thereof.

17. The system of claim 9, wherein the non-biological materials are selected from the group consisting of pesticides, herbicides, and fertilizers.

18. The system of claim 1, wherein the additives are selected from the group consisting of hydroxybenzotriazole, pentafluorophenol and N-hydroxy-5-norboren-endo-2,3-dicarboximide.

* * * * *

UNITED STATES PATENT AND TRADEMARK OFFICE
CERTIFICATE OF CORRECTION

PATENT NO. : 7,163,698 B2  Page 1 of 1
APPLICATION NO. : 10/423536
DATED : January 16, 2007
INVENTOR(S) : Jong Eun Oh et al.

It is certified that error appears in the above-identified patent and that said Letters Patent is hereby corrected as shown below:

Item (73) on the Title page of the patent, the first assignee --Mogam Biotechnology Research Institute (KR)-- and the second assignee --Korea Advanced Institute of Science and Technology (KR)-- should be added.

Signed and Sealed this

Nineteenth Day of June, 2007

JON W. DUDAS
*Director of the United States Patent and Trademark Office*